United States Patent [19]

Roessler et al.

[11] Patent Number: 5,399,219
[45] Date of Patent: Mar. 21, 1995

[54] METHOD FOR MAKING A FASTENING SYSTEM FOR A DYNAMIC FITTING DIAPER

[75] Inventors: Thomas H. Roessler, Menasha; Paul T. Van Gompel, Hortonville; Kathleen A. O'Rourke, Neenah, all of Wis.

[73] Assignee: Kimberly-Clark Corporation, Neenah, Wis.

[21] Appl. No.: 200,593

[22] Filed: Feb. 23, 1994

[51] Int. Cl.⁶ .................... A61F 13/60; A61F 13/58; B32B 31/18
[52] U.S. Cl. ................... 156/259; 156/229; 156/265; 156/269; 156/271; 156/324; 604/389; 604/390; 604/391
[58] Field of Search ............... 156/229, 259, 264, 265, 156/269, 271, 324, 289; 604/389, 390, 391

[56] References Cited

U.S. PATENT DOCUMENTS

| | | |
|---|---|---|
| 2,714,889 | 8/1955 | Chambers . |
| 3,616,114 | 10/1971 | Hamaguchi et al. . |
| 3,862,634 | 1/1975 | Small ................... 604/390 |
| 3,948,267 | 4/1976 | Karami ................ 604/390 |
| 3,948,268 | 4/1976 | Karami ................ 604/390 |
| 4,029,098 | 6/1977 | Karami ................ 604/390 |
| 4,050,462 | 9/1977 | Woon et al. . |
| 4,051,853 | 10/1977 | Egan, Jr. . |
| 4,055,182 | 10/1977 | Mack . |

(List continued on next page.)

FOREIGN PATENT DOCUMENTS

| | | |
|---|---|---|
| 0110010A1 | 6/1984 | European Pat. Off. . |
| 0191355A1 | 8/1986 | European Pat. Off. . |
| 0233704B1 | 8/1987 | European Pat. Off. . |
| 0396050A2 | 11/1990 | European Pat. Off. . |
| 0433951A2 | 6/1991 | European Pat. Off. . |
| 0463276A1 | 1/1992 | European Pat. Off. . |
| 0487758A1 | 6/1992 | European Pat. Off. . |
| 0532034A2 | 3/1993 | European Pat. Off. . |
| 0539032A1 | 4/1993 | European Pat. Off. . |
| 1359810 | 3/1963 | France . |
| 2403036 | 4/1979 | France . |
| 2606257 | 5/1988 | France . |
| 3419621A1 | 11/1985 | Germany . |
| 3419623A1 | 11/1985 | Germany . |
| 069653 | 4/1986 | Israel . |
| 5-65321 | 8/1993 | Japan . |
| 6-11725 U | 2/1994 | Japan . |
| 450816 | 7/1936 | United Kingdom ............ 156/269 |
| 808966 | 2/1959 | United Kingdom . |
| 1379689 | 1/1975 | United Kingdom . |
| 2244422A | 12/1991 | United Kingdom . |
| 2257895A | 1/1993 | United Kingdom . |
| WO90/07426 | 7/1990 | WIPO . |
| WO91/00720 | 1/1991 | WIPO . |

*Primary Examiner*—Jeff H. Aftergut
*Attorney, Agent, or Firm*—Paul Yee

[57] ABSTRACT

A method for forming a plurality of adhesive fastener assemblies includes the step of providing a substantially continuous web of substrate material along a selected, longitudinal machine-direction (132). The substrate web has a laterally extending cross direction (134) which is substantially perpendicular to the machine direction, and has laterally opposed, longitudinally extending side edge regions (142 and 144) thereof. A selected fastening means, such as a layer of primary adhesive (54), is positioned and applied onto a major facing surface (186) of the substrate web (140). A first longitudinally extending web of stiffening material (154) is attached to the major surface of the substrate web (140) at a location which is proximate a first side edge region (142) of the substrate web. A second longitudinally extending web of stiffening material (156) is attached to the major surface of the substrate web (140) at a location which is proximate the second side edge region (144) of the substrate web (140). The web of substrate material and the webs of stiffening material thereby form a substrate composite (192). The substrate web is separated along a longitudinally extending medial region thereof, with a substantially regularly undulating serpentine separation line (158) to provide an opposed pair of fastener tab subassemblies (194 and 196).

22 Claims, 11 Drawing Sheets

U.S. PATENT DOCUMENTS

| | | |
|---|---|---|
| 4,066,081 | 1/1978 | Schaar . |
| 4,074,716 | 2/1978 | Schaar ................................. 604/390 |
| 4,076,663 | 2/1978 | Masuda et al. . |
| 4,237,890 | 12/1980 | Laplanche . |
| 4,286,082 | 8/1981 | Tsubakimoto et al. . |
| 4,522,853 | 6/1985 | Szonn et al. . |
| 4,568,344 | 2/1986 | Suzuki et al. . |
| 4,585,447 | 4/1986 | Karami . |
| 4,595,441 | 6/1986 | Holvoet et al. ..................... 156/265 |
| 4,643,729 | 2/1987 | Laplanche . |
| 4,663,220 | 5/1987 | Wisneski et al. . |
| 4,704,116 | 11/1987 | Enloe . |
| 4,726,971 | 2/1988 | Pape et al. . |
| 4,753,646 | 6/1988 | Enloe . |
| 4,753,649 | 6/1988 | Pazdernik . |
| 4,778,701 | 10/1988 | Pape et al. . |
| 4,787,897 | 11/1988 | Torimae et al. . |
| 4,795,456 | 1/1989 | Borgers et al. . |
| 4,801,480 | 1/1989 | Panza et al. . |
| 4,826,499 | 5/1989 | Ahr . |
| 4,857,067 | 8/1989 | Wood et al. . |
| 4,911,702 | 3/1990 | O'Leary et al. . |
| 4,916,005 | 4/1990 | Lippert et al. . |
| 4,938,753 | 7/1990 | Van Gompel et al. . |
| 4,978,570 | 12/1990 | Heyn et al. . |
| 5,024,672 | 6/1991 | Widlund . |
| 5,032,119 | 7/1991 | Hookano . |
| 5,034,007 | 7/1991 | Igaue et al. . |
| 5,057,097 | 10/1991 | Gesp . |
| 5,092,862 | 3/1992 | Muckenfuhs et al. . |
| 5,106,384 | 4/1992 | Polski ................................. 604/390 |
| 5,110,386 | 5/1992 | Ochi et al. . |
| 5,176,670 | 1/1993 | Roessler et al. . |
| 5,176,672 | 1/1993 | Bruemmer et al. . |
| 5,192,606 | 3/1993 | Proxmire et al. . |
| 5,226,992 | 7/1993 | Morman . |
| 5,288,546 | 2/1994 | Roessler et al. ................. 604/390 X |
| 5,312,387 | 5/1994 | Rossini et al. . |
| 5,330,598 | 7/1994 | Erdman et al. ................. 156/265 X |

FIG. I

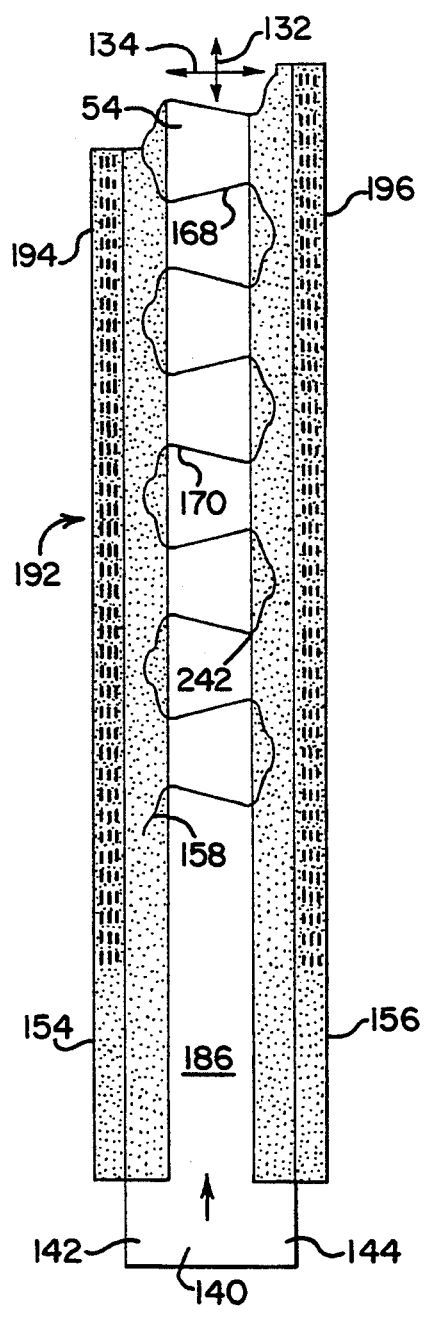
FIG. 4
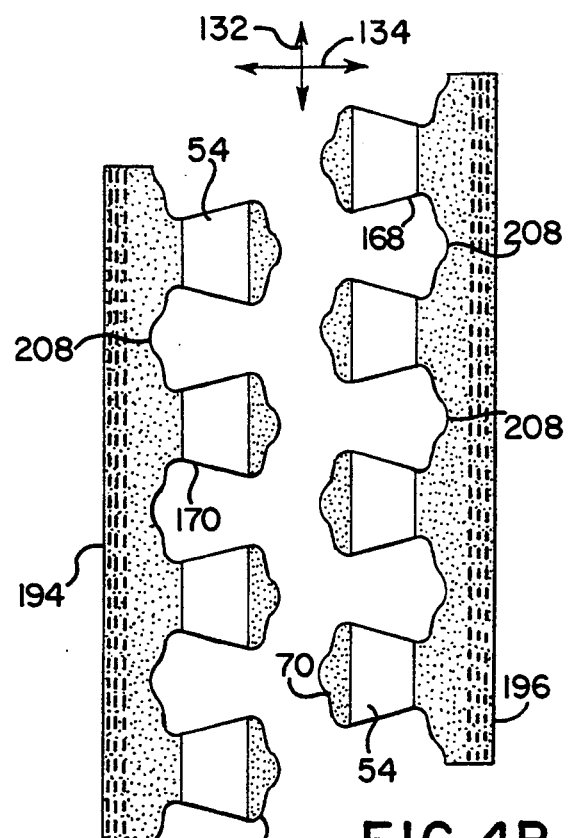
FIG. 4A
FIG. 4B
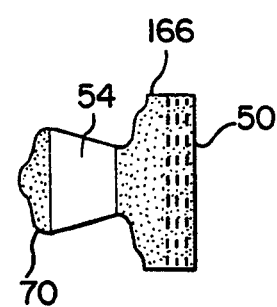
FIG. 4C

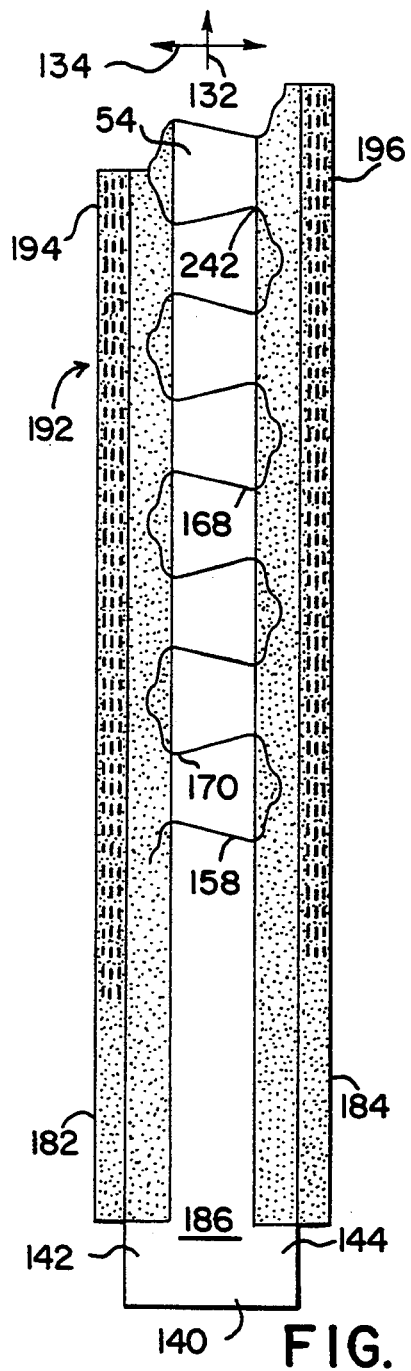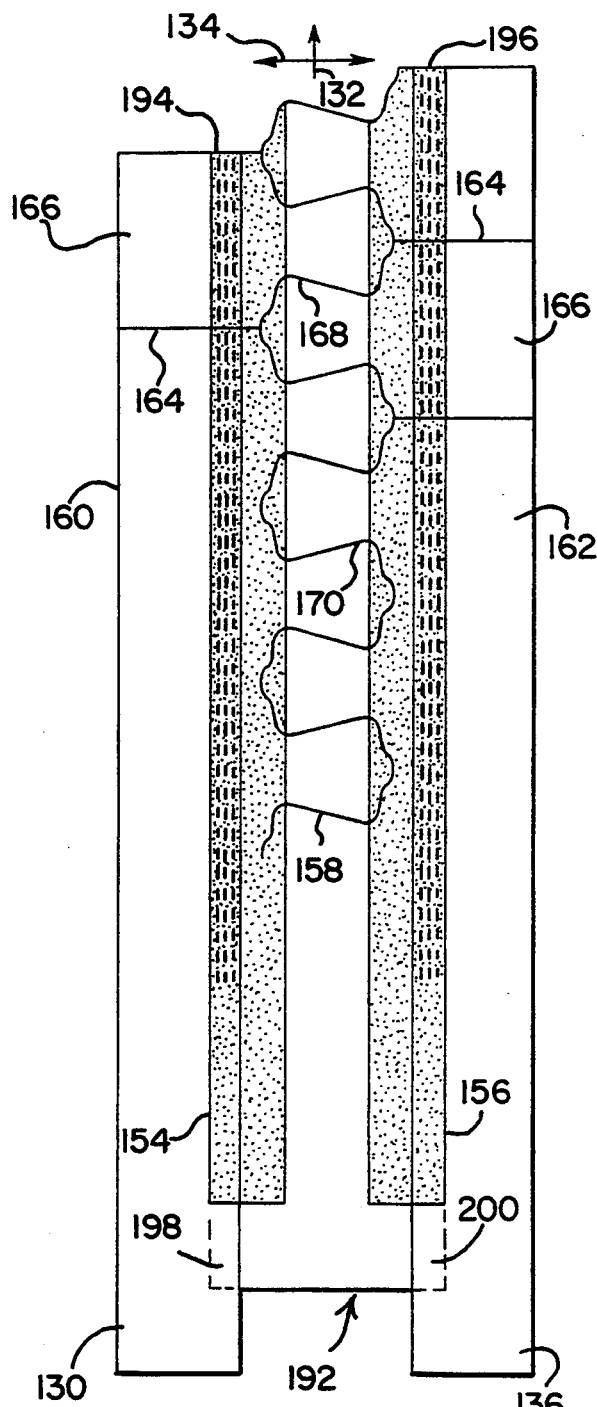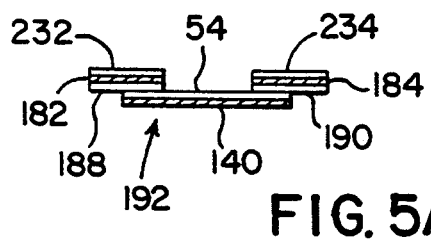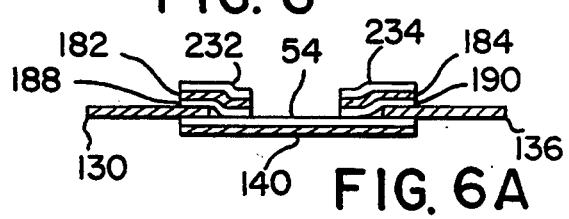

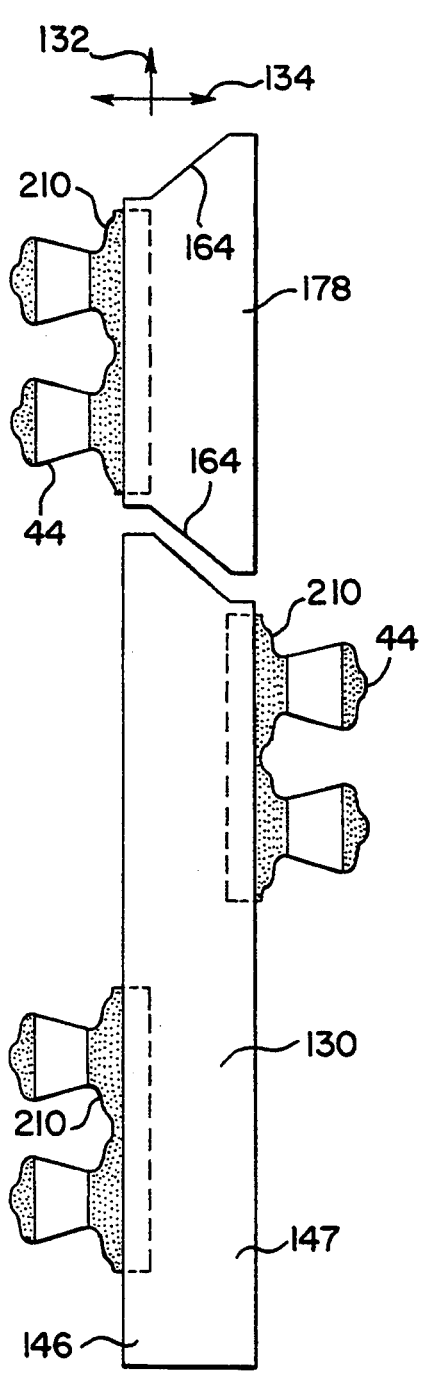
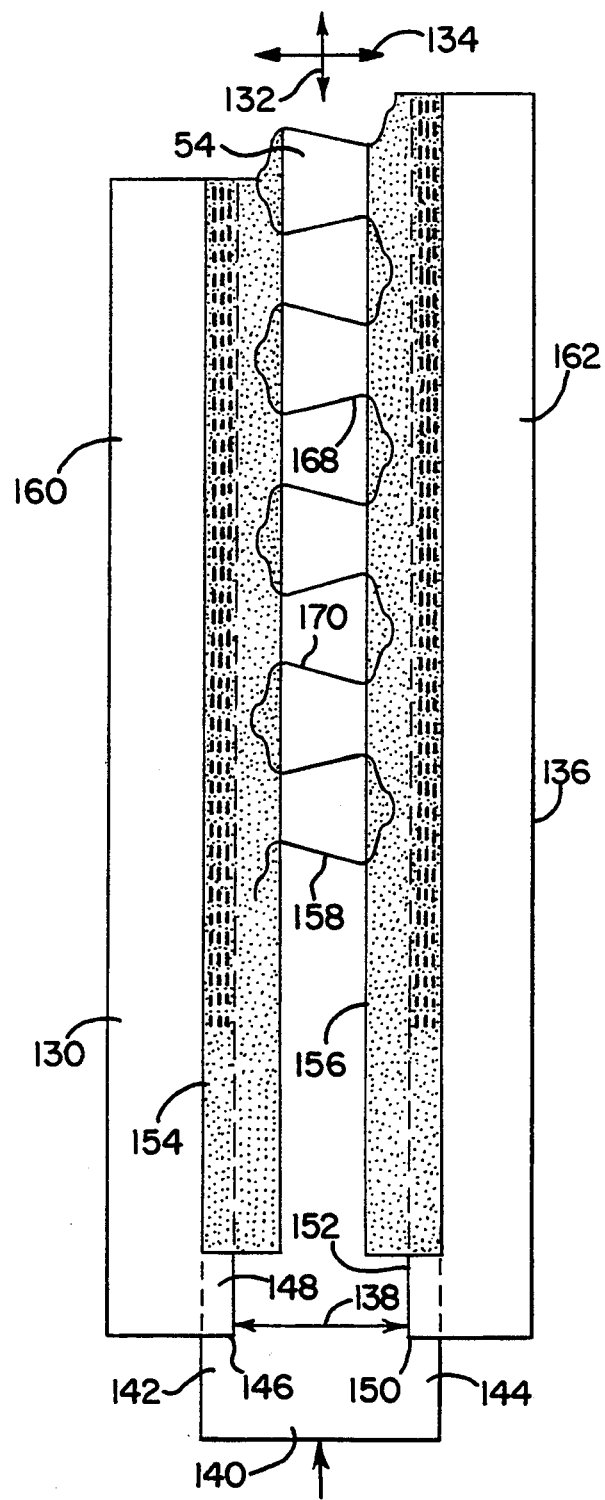
FIG. 9
FIG. 10

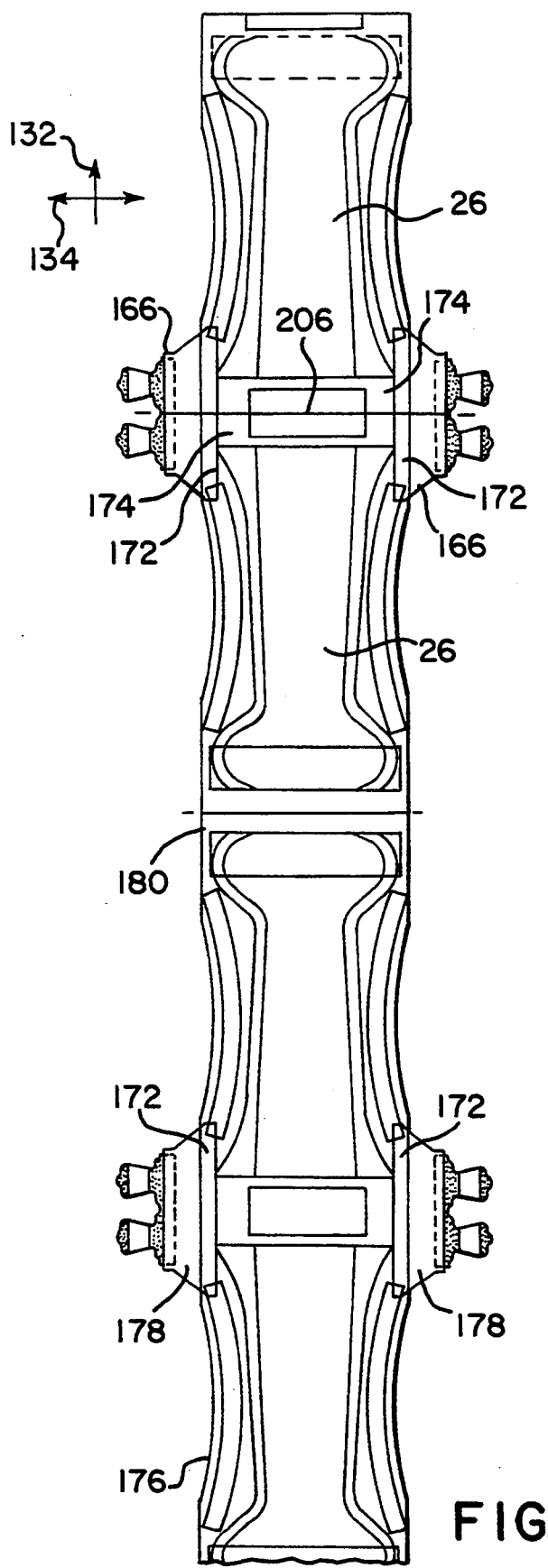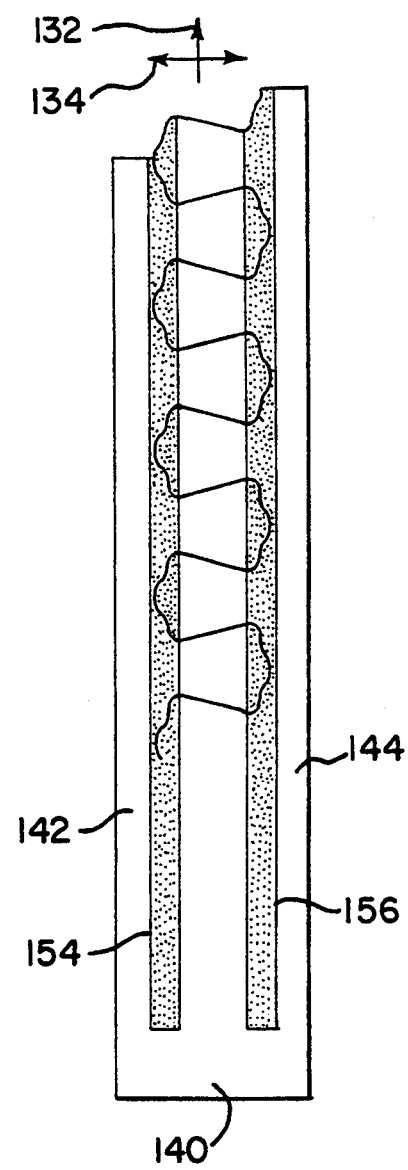

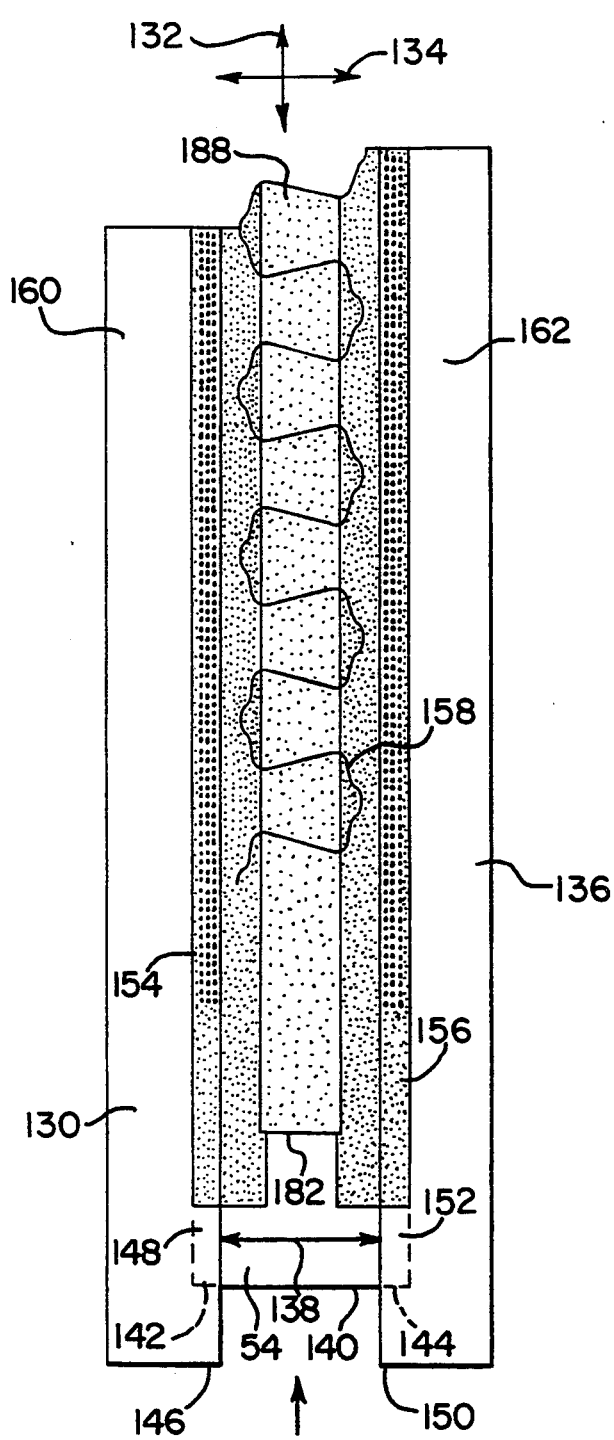
FIG. 12
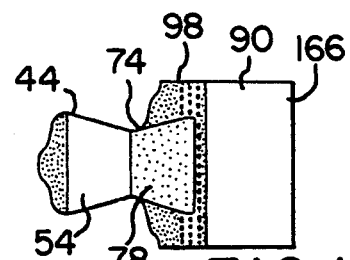
FIG. 12D
FIG. 12C
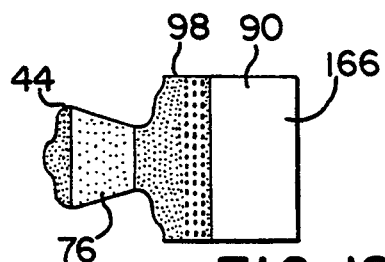
FIG. 12B
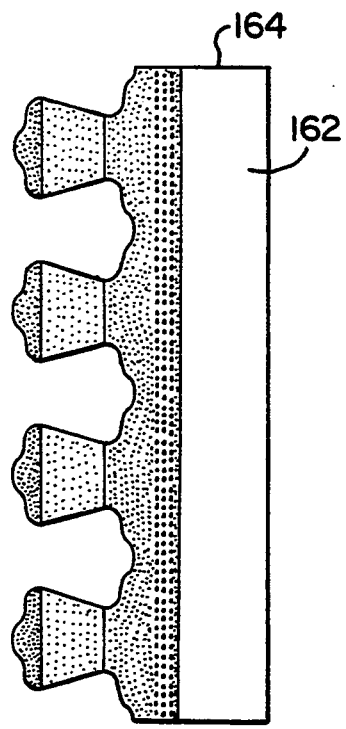
FIG. 12A

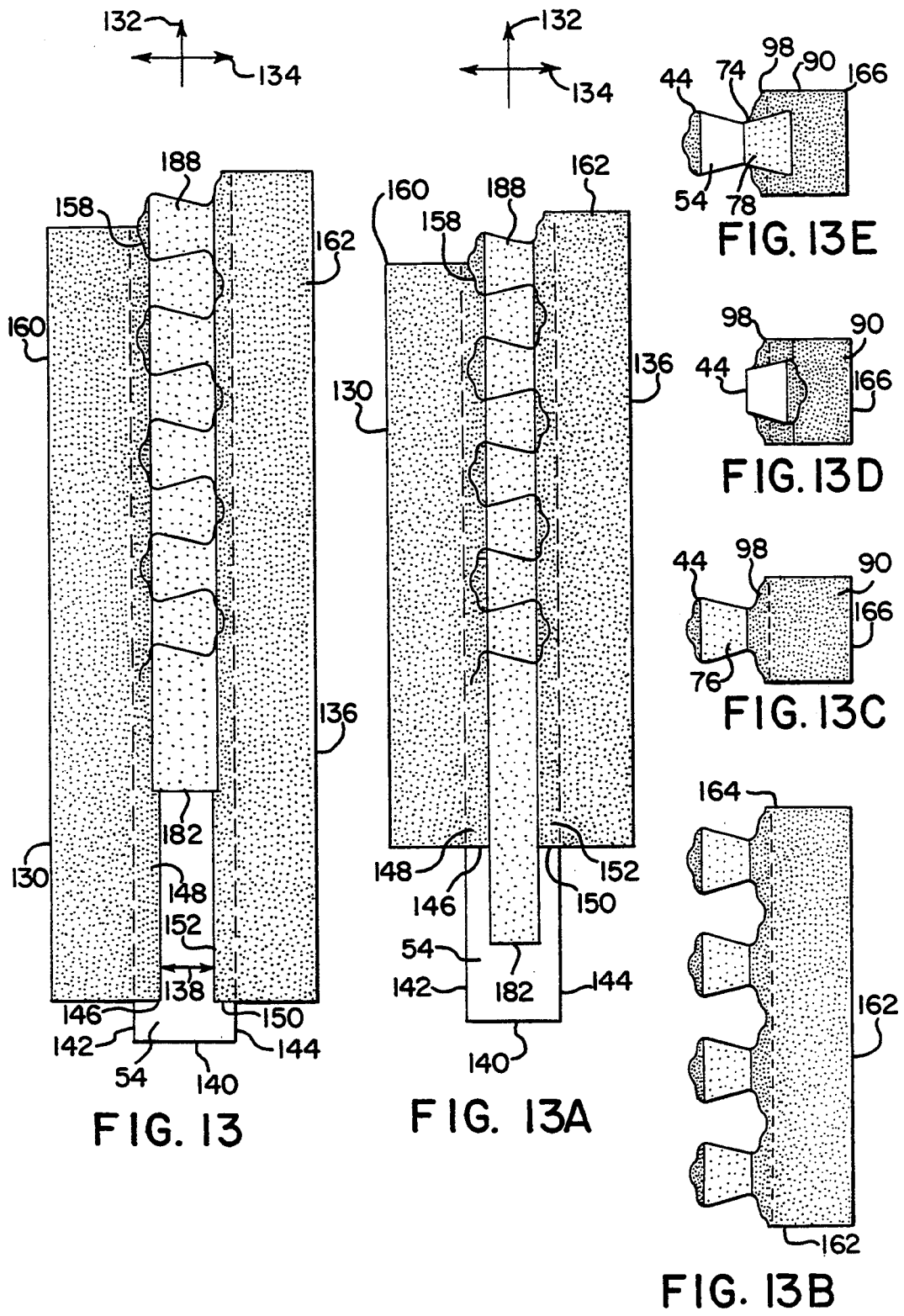

METHOD FOR MAKING A FASTENING SYSTEM FOR A DYNAMIC FITTING DIAPER

FIELD OF THE INVENTION

The present invention relates to fastening systems for disposable garments, such as caps, gowns, diapers, shoe covers, incontinence garments and the like. More particularly, the present invention relates to adhesive tape fastening systems and interlocking, mechanical-type fastening systems for disposable articles, such as gowns, diapers, incontinence garments and the like.

BACKGROUND OF THE INVENTION

Conventional disposable absorbent articles have typically employed adhesive fastening tapes for securing the article on a wearer. For example, see U.S. Pat. No. 2,714,889 issued Aug. 9, 1955, to U. Chambers and U.S. Pat. No. 4,050,462 issued Sep. 27, 1977, to L. Woon et al. Conventional adhesive tape fastening systems have employed adhesive tape tabs which include a non-adhesive section located at the distal free end of the tape tab. This adhesive-free region has typically referred to as a finger tab for facilitating the grasping of the end of the adhesive tape. For example, U.S. Pat. No. 4,055,182 issued Oct. 25, 1977, to R. Mack describes an end tab formed by folding the end region of the tab back onto itself. Other adhesive tape structures have included a finger tab formed by placing a separate piece of material at the terminal free end of the tape member. For example, see U.S. Pat. No. 4,726,971 issued Feb. 23, 1988, to P. Pape et al.; U.S. Pat. No. 3,616,114 issued Oct. 26, 1971, to T. Hamaguchi et al.; U.S. Pat. No. 4,801,480 issued Jan. 31, 1989, to V. Panza et al. Other articles have included a fastening system which extends along substantially the entire length of an ear section of the article. Still other conventional fastening systems have employed tapered fastening tabs where the user's end is relatively wide at the longitudinally extending sides of the diaper, and is tapered to a more narrow width at its distal end. For example, see European Patent 0 233 704 B1 of H. Burkhard et al.

Conventional fastening systems, such as those described above, have not provided an adequate level of dynamic fit in combination with a neat tailored appearance and reliable securement. Processes for producing such conventional fastening systems have not been adequate for producing improved fastening systems that have a greater capability of moving and adjusting to accommodate the stresses and displacements caused by an active wearer. As a result, the conventional methods have not been adequate for producing fastening systems which are configured to exhibit desired levels of reliable securement and comfort.

BRIEF DESCRIPTION OF THE INVENTION

Generally stated, a distinctive method for forming a plurality of fastener assemblies includes the step of providing a substantially continuous web of substrate material along a selected, longitudinal direction. The substrate web has a major facing surface thereof, and has first and second side edge regions thereof. A selected fastening means is provided for on the major facing surface of the substrate web. A first web of stiffening material is attached to the substrate web at a location which is proximate the first side edge region of the substrate web. A second web of stiffening material is attached to the substrate at a location which is proximate the second side edge region of the substrate web. A medial region of the substrate web is separated along an undulating serpentine separation line to provide at least first and second fastener tab subassemblies. In particular configurations, either or both webs of side panel material are constructed of an elastomeric material which is stretchable at least along a cross-deckle direction of the method.

A further process aspect of the invention provided a method for forming a plurality of adhesive fastener assemblies, which includes the step of providing a substantially continuous web of substrate material along a selected, longitudinal machine-direction. The substrate web has a laterally extending cross-direction which is substantially perpendicular to said machine-direction, and has laterally opposed, longitudinally extending side edge regions. A component of a primary fastening means is provided on a major facing surface of the substrate web. A first longitudinally extending web of stiffening material is attached to the substrate web at a location which is proximate a first of the substrate side edge regions, and a second longitudinally extending web of stiffening material is attached to the substrate web at a location which is proximate a second of the substrate side edge regions. The substrate web is separated along a longitudinally extending medial region thereof with a substantially regularly undulating serpentine separation line to provide for an opposed pair of fastener tab subassemblies. At least one of the fastener tab subassemblies is divided along a plurality of division lines which extend substantially laterally across the at least one subassembly to provide a plurality of fastener tab components having an appointed factory bond region thereof. The factory bond regions of a plurality of said fastener tab components are connected to at least one longitudinally extending side edge region of a substantially continuous web of elastomerically stretchable material which is elastomerically stretchable at least along the cross-direction. The elastomerically stretchable web is severed along a plurality of severance lines which extend substantially laterally across the stretchable web to provide for a plurality of composite panel-and-fastener components.

Still another process aspect of the invention provides a method for forming an article having stretch panel fasteners, which includes the step of providing a first, substantially continuous web of elastomerically stretchable material along a selected, longitudinal machine-direction. The material is elastomerically stretchable at least along a laterally extending cross-direction which is substantially perpendicular to the machine-direction. At least a second, substantially continuous web of the elastomerically stretchable material is provided along the machine-direction, and the second web of stretchable material is spaced from the first web of stretchable material by a selected distance along the cross direction. A substantially continuous web of substrate material is provided along the machine-direction at a location which is between the first and second webs of stretchable material. The substrate web has laterally opposed, longitudinally extending side edge regions thereof. A longitudinally extending lateral side edge region of the first web of stretchable material is attached to the first, side edge region of the substrate web to provide a first bonded region. A longitudinally extending lateral side edge region of the second web of stretchable material is attached to the second, side edge region of the substrate web to provide a second bonded region. A first longitudinally extending web of stiffening material is overlapped over the first bonded region and the first stiffening web is connected to the first web of stretchable material and to the substrate web. A second longitudinally extending web of stiffening material is overlapped over the second bonded region and the second stiffening web is connected to the second web of stretchable material and to the substrate web. The substrate web is separated along a longitudinally extending medial region thereof with a substantially regularly undulating serpentine separation line to provide an opposed pair of composite subassemblies. At least one subassembly is divided along a plurality of division lines which extend substantially laterally across the subassembly to provide a plurality of longitudinally paired, combined panel-and-fastener components.

The various process aspects of the present invention can advantageously provide an efficient technique for rapidly producing the taping system of the invention. In particular configurations, the method can be carried out in-line with the process for manufacturing the associated article that employs the tape fastening system, thereby helping to reduce costs.

BRIEF DESCRIPTION OF THE DRAWINGS

The present invention will be more fully understood and further advantages will become apparent when reference is made to the following detailed description of the invention and the drawings, in which:

FIG. 4 representatively shows a top plan view of a process for forming a composite web which can be divided into individual fastener tabs;

FIGS. 4A and 4B representatively shows a top plan view of an opposed pair of fastener tab subassemblies formed from the composite web illustrated in FIG. 4;

FIG. 4C representatively shows a top plan view of a fastener tab formed from one of the fastener tab subassemblies illustrated in FIG. 4;

FIG. 5 representatively shows a top plan view of a process for forming a composite web which can be divided into individual fastener tabs, wherein webs of stiffening material are composed of a release tape material;

FIG. 5A representatively shows a cross-sectional view of the process configuration illustrated in FIG. 5;

FIG. 6 representatively shows a top plan view of a process for forming a composite web which can be divided into individual panel-and-fastener components;

FIG. 6A representatively shows a cross-sectional view of the process illustrated in FIG. 6;

FIG. 9 representatively shows a top plan view of an aspect of the invention which is configured to form a selected plurality of longitudinally-paired, panel-and-fastener components;

FIG. 10 representatively shows another alternative method for producing a composite web which can be divided into individual panel-and-fastener components;

FIG. 11 representatively shows a top plan view of an aspect of the invention which includes the step of connecting longitudinally-paired fastener tab sets to appointed waistband sections of an article web;

FIG. 12 representatively shows a top plan view of an aspect of the invention which includes the step of disposing a web of release tape material onto an adhesive-bearing surface of a substrate web;

FIG. 12A representatively shows a top plan view of a panel-and-fastener subassembly formed from the method illustrated in FIG. 12;

FIG. 12B representatively shows a top plan view of a panel-and-fastener component formed from the subassembly illustrated in FIG. 12A;

FIG. 12C representatively shows a top plan view of the panel-and-fastener component illustrated in FIG. 12B where the fastener tab has been folded over into its storage configuration;

FIG. 12D representatively shows a top plan view of the panel-and-fastener component illustrated in FIG. 12C where the fastener tab has been unfolded from its storage configuration into an arrangement ready for forming a desired user-bond;

FIG. 13 representatively shows a top plan view of another aspect of the invention which includes the step of disposing a web of release tape material onto an adhesive-bearing surface of a substrate web;

FIG. 13A representatively shows a top plan view of a further aspect of the invention which includes the step of disposing a narrower web of release tape material onto an adhesive-bearing surface of a substrate web;

FIG. 13B representatively shows a top plan view of a panel-and-fastener subassembly formed from the method illustrated in FIG. 13A;

FIG. 13C representatively shows a top plan view of a panel-and-fastener component formed from the subassembly illustrated in FIG. 13B;

FIG. 13D representatively shows a top plan view of the panel-and-fastener component illustrated in FIG. 13C where the fastener tab has been folded over into its storage configuration;

FIG. 13E representatively shows a top plan view of the panel-and-fastener component illustrated in FIG. 13D where the fastener tab has been unfolded from its storage configuration into an arrangement ready for forming a desired user-bond;

FIG. 15 representatively shows a top plan view of an aspect of the invention which includes the steps of connecting first and second longitudinally extending webs of stiffening material to a major facing surface of a substrate web at locations which are proximate first and second side edge regions of the substrate web, and are laterally, inwardly spaced from each of the corresponding first and second side edge regions of the substrate web.

DETAILED DESCRIPTION OF THE INVENTION

The various embodiments of the invention will be described in the context of a disposable absorbent article, such as a disposable diaper. It is, however, readily apparent that the present invention could also be employed with other articles, such as caps, gowns, shoe covers, feminine care articles, incontinence garments and the like.

Typically, disposable articles are intended for limited use and are not intended to be laundered or otherwise cleaned for reuse. For example, a disposable diaper is discarded after it has become soiled by the wearer.

Figure 1:
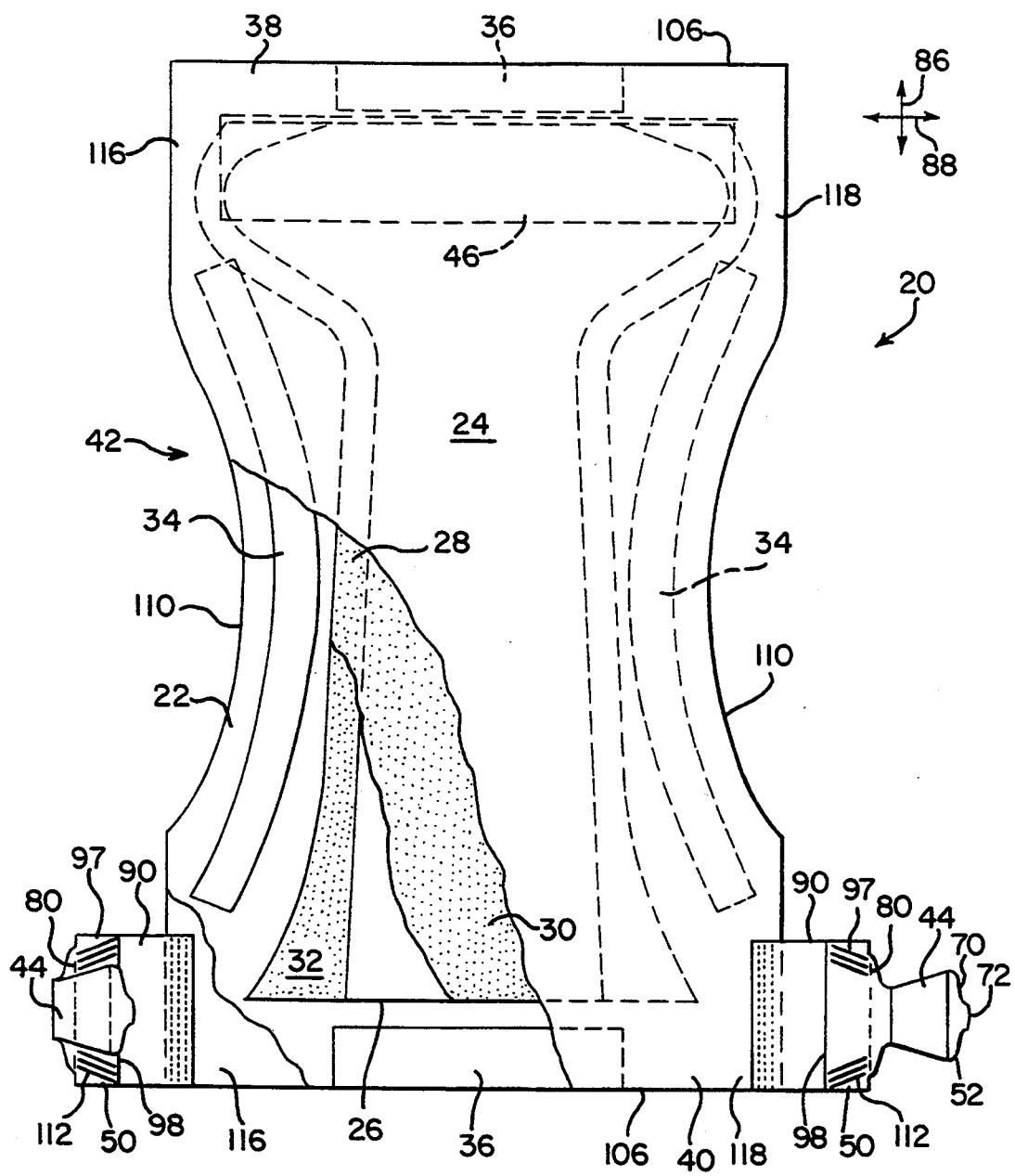
FIG. 1 representatively shows a top plan view of an article and fastening system which can be produced with the method of the present invention.
Figure 2:
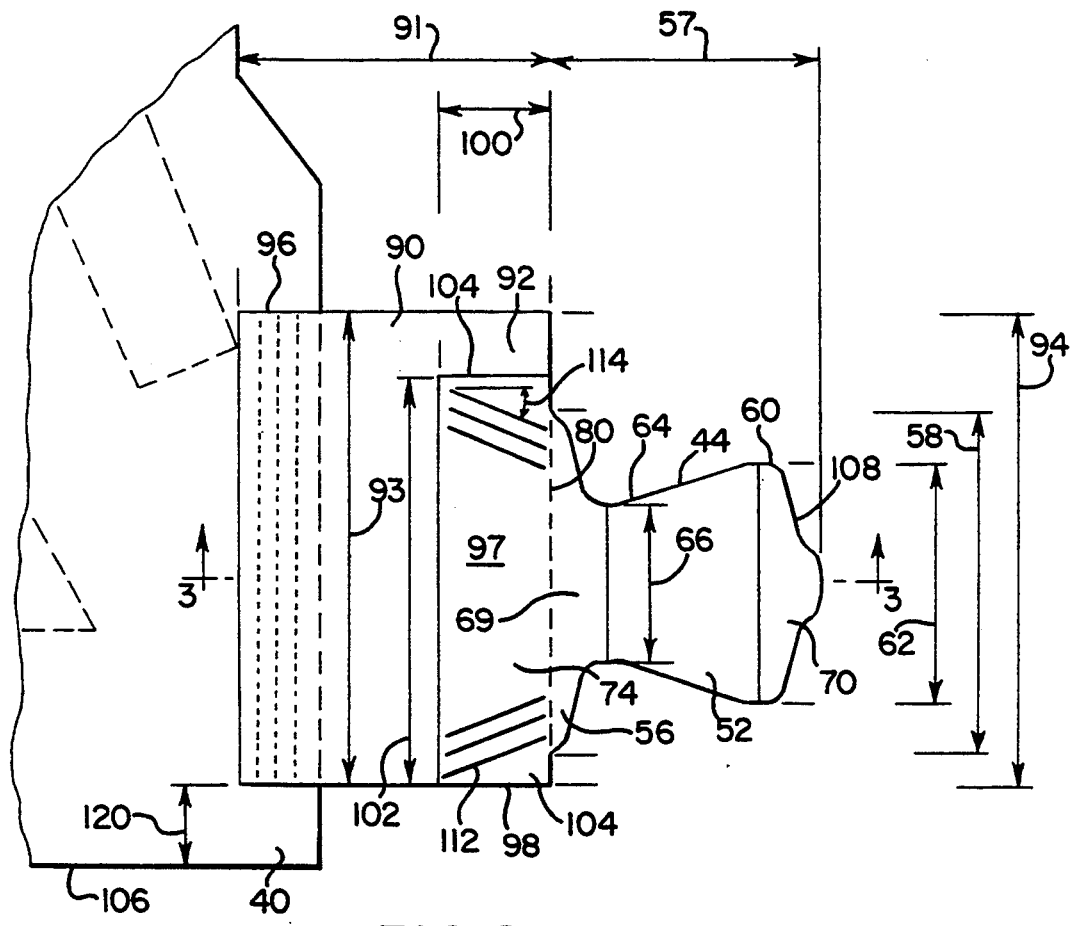
FIG. 2 representatively shows a top plan view of a fastening system having a panel-and-fastener component which can be produced with the method of the present invention.

The method of the present invention can be employed to produce a plurality of selected panel-and-fastener components for various articles, such as a disposable diaper 20. With reference to FIGS. 1 and 2, the representative diaper 20 is shown in its fully extended condition with all of the elasticized gathers stretched out and removed. The article has a first waistband section, such as rear waistband section 40, a second waistband section, such as front waistband section 38, and an intermediate section 42 which interconnects the first and second waistband sections. The article comprises a backsheet layer 22, and a pair of side panels 90, each of which extends laterally from opposed lateral ends of at least one waistband section of backsheet 22. Each of the side panels includes a terminal free end region 92 which has a predetermined length dimension 94 thereof. Each side panel also has a width 91 and a base length 93. A stress beam section 98 is connected to each of the side panels 90 along its free end region 92, and the stress beam section provides for a relatively high Gurley stiffness value, such as a Gurley stiffness value of at least about 20 mg. The stress beam section also has a length dimension 102 which is at least a significant substantial percentage, such as about 33 percent, of the length 94 of the free end region 92 of the side panel. A fastening tab 44 is connected to each of the stress beam sections and is arranged to extend laterally from each of the side panels 90 for securing the waistband sections of the article about a wearer during the use of the article. In particular configurations of the invention, the fastening tab can have a base length 58 which is not more than a selected limited percentage, such as about 90 percent, of the length 102 of the stress beam section 98.

The disposable diaper 20 has a first waistband section, such as rear waistband section 40, a second waistband section, such as front waistband section 38, and an intermediate section 42 which interconnects the first and second waistband sections. The article comprises a backsheet layer 22, and a fastening means, such as fastening tab 44, operably connected to opposed lateral ends of at least one waistband portion 40 or 38 of the backsheet layer for securing the waistband sections of the article about a wearer during the use of the article. The fastening means has a factory bond section 50, a user bond section 52, and a seam section 69 which is located between the factory bond and user bond sections. The user bond section has a length dimension, such as fastening tab length 62, which is larger than a length dimension of said seam section. Depending upon the particular tab configuration, the seam section length may correspond to the base length 58 or the intermediate length 66 of the fastening tab, as appropriate.

An aspect of the invention can provide a fastener article which comprises a tab substrate 48 having a factory bond section 50, a user bond section 52, and a seam section 69 which is located between the factory bond and user bond sections. The user bond section has a length dimension, such as fastening tab length 62, which is larger than a length dimension of the seam section. Depending upon the particular tab configuration, the seam section length may correspond to the base length 58 or to the intermediate length 66 of the fastener tab, as appropriate.

In the various configurations of the invention, diaper 20 can further include a liquid permeable topsheet layer 24 superposed in facing relation with the backsheet layer, and an absorbent body 26 interposed between the backsheet and topsheet layers.

Diaper 20 defines a longitudinally extending length dimension 86 and a laterally extending width dimension 88, as representatively shown in FIG. 1, and may have any desired shape, such as rectangular, I-shaped, a generally hourglass shape, or a T-shape. With the T-shape, the crossbar of the "T" may comprise the front waistband portion of the diaper or may alternatively comprise the rear waistband portion of the diaper.

Backsheet 22 can generally provide an outer cover member of the article and may be composed of a liquid permeable material, but preferably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. Backsheet 22 prevents the exudates contained in absorbent body 26 from wetting articles, such as bedsheets and overgarments, which contact diaper 20. In particular embodiments of the invention, backsheet 22 is a polyethylene film having a thickness of from about 0.012 millimeters (0.5 mil) to about 0.051 millimeters (2.0 mils). In the shown embodiment, the backsheet is a film having a thickness of about 1–1.5 mil. For example, the backsheet film can have a thickness of about 1.25 mil. Alternative constructions of the backsheet may comprise a woven or nonwoven fibrous web layer which has been totally or partially constructed or treated to impart the desired levels of liquid impermeability to selected regions that are adjacent or proximate the absorbent body. Backsheet 22 typically provides the outer cover of the article. Optionally, however, the article may comprise a separate outer cover member which is in addition to the backsheet.

Backsheet 22 may alternatively be composed of a micro-porous, "breathable" material which permits gases, such as water vapor, to escape from absorbent body 26 while substantially preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film can be a PMP-1 material, which is available from Mitsui Toatsu Chemicals, Inc., a company having offices in Tokyo, Japan; or an XK0-8044 polyolefin film available from 3M Company of Minneapolis, Minn. The backsheet may also be embossed or otherwise be provided with a matte finish to exhibit a more aesthetically pleasing appearance.

The size of backsheet 22 is typically determined by the size of absorbent body 26 and the particular diaper design selected. Backsheet 22, for example, may have a generally T-shape, a generally I-shape or a modified hourglass shape, and may extend beyond the terminal edges of absorbent body 26 by a selected distance.

Topsheet 24 presents a body-facing surface which is compliant, soft-feeling, and non-irritating to the wearer's skin. Further, topsheet 24 can be less hydrophilic than absorbent body 26, and is sufficiently porous to be liquid permeable, permitting liquid to readily penetrate through its thickness to reach the absorbent body. A suitable topsheet 24 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 24 is typically employed to help isolate the wearer's skin from liquids held in absorbent body 26. The topsheet materials may be composed of a substantially hydrophobic material, and the hydrophobic material may optionally be treated with a surfactant or otherwise processed to impart a desired level of wettability and hydrophilicity. For example, the topsheet can be treated with about 0.28% Triton X-102 surfactant.

Various woven and nonwoven fabrics can be used for topsheet 24. For example, the topsheet may be composed of a meltblown or spunbonded web of polyolefin fibers. The topsheet may also be a bonded-carded-web composed of natural fibers, synthetic fibers or combinations thereof.

For the purposes of the present description, the term "nonwoven web" means a web of material which is formed without the aid of a textile weaving or knitting process. The term "fabrics" is used to refer to all of the woven, knitted and nonwoven fibrous webs.

In the shown embodiment of diaper 20, for example, topsheet 24 and backsheet 22 can be generally coextensive and have length and width dimensions which are generally larger than the corresponding dimensions of absorbent body 26. Topsheet 24 is associated with and superimposed on backsheet 22, thereby defining the periphery of diaper 20.

Topsheet 24 and backsheet 22 are connected or otherwise associated together in an operable manner. As used herein, the term "associated" encompasses configurations in which topsheet 24 is directly joined to backsheet 22 by affixing topsheet 24 directly to backsheet 22, and configurations wherein topsheet 24 is indirectly joined to backsheet 22 by affixing topsheet 24 to intermediate members which in turn are affixed to backsheet 22. Topsheet 24 and backsheet 22 can be affixed directly to each other in the diaper periphery by attachment means (not shown) such as an adhesive bonds, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet 24 to backsheet 22. It should be readily appreciated that the above-described attachment means, in desired combinations, may also be employed to interconnect and assemble together the other component parts of the article.

Absorbent body 26 can comprise an absorbent pad composed of selected hydrophilic fibers and high-absorbency particles. The absorbent body is positioned between topsheet 24 and backsheet 22 to form diaper 20. The absorbent body has a construction which is generally compressible, conformable, non-irritating to the wearer's skin, and capable of absorbing and retaining liquid body exudates. It should be understood that, for purposes of this invention, the absorbent body may comprise a single, integral piece of material, or alternatively, may comprise a plurality of individual separate pieces of material which are operably assembled together.

Various types of wettable, hydrophilic fibrous material can be used to form the component parts of absorbent body 26. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes materials the surfaces of which are wetted by the contact of aqueous liquids. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System. When measured with this system in accordance with the procedure described in detail herein below, fibers having contact angles less than 90° are designated "wettable", while fibers having contact angles greater than 90° are designated "nonwettable".

Absorbent body 26 can comprise a matrix of hydrophilic fibers, such as a web of cellulosic fluff, mixed with particles of high-absorbency material. In particular arrangements, absorbent body 26 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outerside of the absorbent structure. Suitable z-gradient configurations are described in U.S. Pat. No. 4,699,823 issued Oct. 13, 1987 to Kellenberger et al., the disclosure of which is incorporated herein by reference to the extent that it is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outerside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarson et al. in U.S. Pat. No. 3,902,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

To improve the containment of the high-absorbency material, absorbent body 26 can include an improved overwrap, such as wrap sheet 28, placed immediately adjacent and around absorbent body 26. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrap which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

Diaper 20 can also include a surge management layer 84 which helps to decelerate and diffuse surges of liquid that may be introduced into the absorbent body of the article. In the illustrated embodiment, for example, surge layer 84 can be located on an inwardly facing body side surface of topsheet layer 24. Alternatively, surge layer 84 may be located adjacent to an outer side surface of topsheet 24. Accordingly, the surge layer would then be interposed between topsheet 24 and absorbent body 26.

Leg elastic members 34 are located in the lateral side margins 110 of diaper 20 and are arranged to draw and hold diaper 20 against the legs of the wearer. The elastic members are secured to diaper 20 in an elastically contractible condition so that in a normal under strain configuration, the elastic members effectively contract against diaper 20.

In the embodiment illustrated in FIG. 1, leg elastic members 34 extend essentially along the complete length of the intermediate crotch region 42 of diaper 20. Alternatively, elastic members 34 may extend the entire length of diaper 20, or any other length suitable providing the arrangement of elastically contractible lines desired for the particular diaper design.

Elastic members 34 may have any of a multitude of configurations. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 20 with sprayed or swirled patterns of hotmelt adhesive.

In the illustrated embodiments of the invention, leg elastic members 34 may comprise a carrier sheet (not shown) to which are attached a grouped set of elastics composed of a plurality of individual elastic strands 39. The elastic strands may intersect or be interconnected, or be entirely separated from each other. The carrier sheet may, for example, comprise a 0.002 cm thick film of unembossed polypropylene material. The elastic strands can, for example, be composed of Lycra elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, leg elastics 34 may be generally straight or optionally curved. For example, the curved elastics can be inwardly bowed toward the longitudinal centerline of the diaper with the innermost point (or apex, relative to the cross-direction of the article) of the set of curved elastic strands positioned approximately 0.75–1.5 inches inward from the outer most edge of the set of elastic strands. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance within the range of about 0–8 cm toward either the front or rear waistband of the diaper to provide desired fit and appearance.

In the shown embodiment, diaper 20 includes a waist elastic 36 positioned in the longitudinal margins of either or both of front waistband 38 and rear waistband 40. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the disclosure of which is hereby incorporated by reference to the extent that it is consistent (not contradictory) herewith.

Diaper 20 can also include a pair of elasticized containment flaps 82 which extend longitudinally along the length dimension 86 of the diaper. The containment flaps are typically positioned laterally inboard from leg elastics 34, and substantially symmetrically placed on each side of the lengthwise, longitudinal centerline of the diaper. Examples of suitable containment flap constructions are described in U.S. Pat. No. 4,704,116 issued Nov. 3, 1987, to K. Enloe, the disclosure of which is hereby incorporated by reference to the extent that it is consistent herewith. The containment flaps may be composed of a wettable or a non-wettable material, as desired.

In an optional, alternative embodiment of the invention, diaper 20 may include elasticized waist flaps, such as those described in U.S. Pat. No. 4,753,646 issued Jun. 28, 1988, to K. Enloe, the disclosure of which is hereby incorporated by reference to the extent that it is consistent herewith. Similar to the construction of the containment flaps, the waist flaps may be composed of a wettable or non-wettable material, as desired. The waist and/or containment flap materials may be fluid impermeable, permeable to gas, or permeable to both gas and liquid.

Absorbent article structures suitable for use with the present invention are described in U.S. patent application Ser. No. 07/757,778 of D. Proxmire et al., filed Sep. 11, 1991, and entitled "ABSORBENT ARTICLE HAVING A LINER WHICH EXHIBITS IMPROVED SOFTNESS AND DRYNESS, AND PROVIDES FOR RAPID UPTAKE OF LIQUID" (Attorney Docket No. 9932), now U.S. Pat. No. 5,192,606 issued Mar. 9, 1993, the disclosure of which is hereby incorporated by reference to the extent that it is consistent with the present specification. Other absorbent article structures suitable for use with the present invention are described in U.S. patent application Ser. No. 07/757,760; "THIN ABSORBENT ARTICLE HAVING RAPID UPTAKE OF LIQUID"; of W. Hanson et al. filed Sep. 11, 1991 (Attorney Docket No. 9922), the disclosure of which is hereby incorporated by reference to the extent that it is consistent herewith.

To provide a refastenable adhesive taping system, diaper 20 can include a supplemental landing zone patch 46, which provides a target zone for receiving an adhesive attachment of tape fasteners 44 thereon. In the illustrated embodiment of the invention, landing zone patch 46 is positioned on the outward surface of backsheet 22 and is located on the second, front waistband portion 38 of the diaper. Landing zone patch 46 is constructed of a suitable material, such as polypropylene, polyester, or the like, and is configured and arranged to accept a secure adhesion of tape fasteners 44. In addition, the landing zone patch and the tape fasteners are cooperatively constructed and arranged to provide a releasable adhesion which allows the tape fastener to be removed from the landing zone patch for repositioning and re-adhesion without tearing or excessively deforming the material of backsheet 22. For example, a suitable tape landing zone construction is described in U.S. Pat. No. 4,753,649 issued to Pazdernik, the disclosure of which is hereby incorporated by reference to the extent that it is consistent herewith.

In various embodiments of the invention, a tape fastener 44 can be located at either or both of lateral end regions 116 and 118 of either or both of waistbands 38 and 40, respectively. The representatively shown embodiment has the tape fasteners located at the terminal side edges of rear waistband 40.

Articles which include separate panel-and-fastener sections which can be constructed with the method of the present invention are described in copending U.S. patent application Ser. No. 168,615 entitled "DYNAMIC FITTING DIAPER" filed Dec. 16, 1993 by T. Roessler et al. (Attorney Docket No. 10,961). The disclosure of this document is hereby incorporated by reference to the extent that it is consistent herewith.

With reference to FIGS. 1 and 2, for example, each side panel 90 extends laterally from the opposed lateral ends of at least one waistband portion of backsheet 22, such as rear waistband portion 40, to provide terminal side sections of the article. In addition, each side panel can substantially span from a laterally extending, terminal waistband edge 106 to approximately the location of a corresponding leg opening section of the diaper. Diaper 20, for example, has a laterally opposed pair of leg openings formed by appointed, medial sections of the shown pair of longitudinally extending, side edge regions 110. In the various configurations of the invention, the side panels may be integrally formed with a selected diaper component. For example, side panels 90 can be integrally formed from the layer of material which provides backsheet layer 22, or may be integrally formed from the material employed to provide topsheet 24. In alternative configurations, the side panels 90 may be separate members that are connected to backsheet 22, to topsheet 24, in between the backsheet and topsheet, or combinations thereof.

In particular aspects of the invention, each of the side panels 90 may be formed from a separate piece of material which is then suitably assembled and attached to the selected front and/or rear waistband portion of the diaper article. In the illustrated embodiments of the invention, for example, side panels 90 are attached to the rear waistband portion of backsheet 22, and can be operably attached to either or both of the backsheet and topsheet components of the article. The side panels extend laterally to form a pair of opposed waist-flap sections of the diaper, and are attached with suitable connecting means, such as adhesive bonding, thermal bonding, ultrasonic bonding, clips, staples, sewing or the like.

As previously mentioned, various suitable constructions can be employed to attach the side panels 90 to the selected waistband portions of the article. Where the side panels are composed of an elastomeric material, for example, suitable constructions for securing a pair of elastomeric, stretchable members to the lateral, side portions of an article to extend laterally outward beyond the opposite side regions of the outer cover and liner components of an article can be found in U.S. Pat. No. 4,938,753 issued Jul. 3, 1990 to P. VanGompel et al., the disclosure of which is hereby incorporated by reference to the extent that it is consistent herewith.

In conventional fastening systems, the fastening stress is applied to the factory bond between fastening tab 44 and the side sections of rear waistband 40 substantially across the base length 58 of the fastening tab. As a result, relatively low levels of stress are applied to the regions of the ear sections that are longitudinally adjacent to the side edges of the fastening tab. As a result, the longitudinally adjacent regions tend to wrinkle and curl away from the body of the wearer. The wrinkling and curling can be unsightly and can create gaps along the waistband and along the leg opening region of the diaper through which waste materials may leak from the diaper. Attempts to address this problem have employed complex fastening systems which extend along substantially the entire free edge length of the ear sections of the article. Other attempts to address this problem have employed multiple fastening tapes or a large, wide fastening tab. The wide fastening tabs or tapered fastening tabs have transmitted excessive stresses to the user-bond securement section of the fastening system. Such stresses can tend to undesirably disconnect the user bond portion of the fastening system when the wearer shifts and moves about. In addition, such configurations may not sufficiently conform and adjust to the movements of the wearer, and can result in excessive irritation of the wearer's skin.

To help address the problems associated with conventional fastening systems such as those described above, the present invention can advantageously provide for a distinctive reinforcement, stress beam section 98. The stress beam can disperse and dissipate the fastening forces across the length of each side panel 90. In addition, the stress beam section can provide for a sufficient stiffening and reinforcement of its associated waistband section to help prevent undesired and excessive wrinkling, necking-down or folding-over of the lateral end of the waistband or side panel during the use of the article.

In the various configurations of the invention, stress beam section 98 can be integrally formed from the same material employed to form the side panel 90 associated therewith. For example, a portion of the free end of a side panel may be doubled over one or more times along longitudinally extending fold lines to generate an operable stress beam section. Alternatively, the stress beam section can be provided by densifying or embossing a selectively sized and shaped region of side panel 90 to an extent which provides operable levels of strength and stiffness.

In other arrangements of the invention, stress beam section 98 can include a stiffening or reinforcement member provided by a selectively shaped and sized region of material which is integrally formed with fastening tab substrate 48. Alternatively, the stress beam section can include a separate stiffening or reinforcement member 97 which is appropriately configured, and is assembled to the free end region of the side panel. For example, the stress beam section can be provided for by a suitably sized and shaped piece of material attached to a suitable surface of each side panel 90, such as an inward bodyside surface of each panel. The material may be composed of a polymer film, a nonwoven fabric, a woven fabric or the like, as well as combinations thereof. In a particular configuration, the stress beam section can include a stiffening member composed of the material employed to construct release tape material 74 and/or fastening tab substrate 48. In the various configurations of the invention the stress beam section can be substantially non-extensible and/or substantially non-elastomeric.

With reference to FIG. 2, a stress beam section 98 can be operably connected to each side panel 90 along the free end region 92 of the side panel with suitable attaching means, such as adhesive bonding, thermal bonding, ultrasonic bonding, clips, staples, sewing or the like. The stress beam section has a laterally extending, cross-directional width dimension 100 and a longitudinally extending length dimension 102. To obtain desired performance, it can be advantageous to position stress beam section 98 at a medial location along the length of side panel 90. In the shown embodiment, for example, the stress beam section is substantially centered along the longitudinal length of the free end section of the side panel. A particular aspect of the invention can be configured to employ a separate piece of material which operatively forms a member that overlaps the material of side panel 90 to provide for the desired stress beam section 98.

In other aspects of the invention, stress beam section 98 extends along the longitudinal length of side panel 90 to be substantially coterminous with the laterally extending waistband edge 106 of the article. In the illustrated embodiment, fastening tab 44 is approximately centered along the length of stress beam section 98. Alternatively, the location of fastening tab 44 may be offset longitudinally of the diaper by a selected distance away from the lengthwise center of stress beam section 98.

A fastening means, such as provided by fastening tape tab 44, is operably connected to each of the side panels 90. In the illustrated configuration, the juncture section along which fastening tab 44 intersects the terminal side edge of panel 90 provides a relatively narrowed panel juncture region 80. The connection may be accomplished with suitable attaching means, such as adhesive bonding, thermal bonding, ultrasonic bonding, clips, staples, sewing or the like. Alternatively, the fastening tab substrate may be integrally formed from the material employed to form stress beam section 98. In optional configurations, the fastening tab may be directly or indirectly connected to the stress beam section 98 associated with the respective side panel. For example, the fastening tab 44 may indirectly connect to its associated stress beam section 98 by way of an intervening section of side panel 90.

In the illustrated embodiments of the invention, the components of the fastening means cooperate to secure the front and rear waistband portions of the article about a wearer. In particular, the rear waistband section of the shown embodiment overlaps the front waistband section of the article and the fastening means operably attaches to appointed regions of the front waistband portion.

Fastening tab 44 has a longitudinally extending length dimension and a laterally extending width dimension. In addition, the fastening tab has a base section 56, a user bond end section 60 and an intermediate section 64 which interconnects the base and end sections. Base section 56 has a longitudinal length dimension 58, end section 60 has a longitudinal length dimension 62, and intermediate section 64 has a longitudinal length dimension 66.

In particular aspects of the invention, fastening tab 44 has, along its respective panel juncture region 80, a base length 58 which is not more than about 90 percent of the length 102 of stress beam section 98. Alternatively, the fastening tab base length is not more than about 80 percent of the stress beam section length, and optionally is not more than about 50 percent of the stress beam section length to provide desired performance. In other aspects of the invention, fastening tab 44 has a base length 58 which is not less than about 1 percent of the length 102 of stress beam section 98. Alternatively, the base length is not less than about 5 percent of the stress beam section length, and optionally is not less than about 20 percent of the stress beam section length to provide desired benefits. Accordingly, when the fastening means is employed to secure the article on the wearer, the end sections 104 of the stress beam section are not further attached to the front waistband of the article by the operation of securing the article on the wearer. As a result, the unattached end sections 104 can advantageously slide, bend and otherwise move relative to the secured portions of the article without excessively disturbing the securing attachment between the user bond section of the fastening tab and the appointed securement zone of the article.

In the illustrated embodiments length 58 of the base section 56 of fastening tab 44 is relatively larger than the length 66 of the fastening tab intermediate section 64. Alternatively, however, base length 58 may be equal to or less than the intermediate section length 66. In either case, the construction of the fastening system of the invention can provide a seam section 69 the fastening tab which is positioned between stress beam section 98 and the user bond section 52 of the fastening tab. As determined when the fastening tab in its relaxed and substantially untensioned condition, the tab seam section generally represents the narrowest region of the fastening tab with respect to those portions of the fastening tab that are spaced from the terminal end sections of the tab. Seam section 69 can advantageously provide a relatively more flexible pivot region which can facilitate a freer, less restricted relative movement between the stress beam portion of the fastening system and user bond portion of the fastening tab. As a result, the stress beam 98 can operate to help maintain the desired waistband appearance and good fit during the movements of the wearer, and the user bond section 52 can maintain a more reliable securement with less occurrence of undesired pop-opens. The seam section can help isolate the user bond section of the fastening system from the self-adjusting movements of the side panels 90 and the stress beam sections of the fastening system. In the shown embodiment, the seam section 69 is composed of a substantially non-extensible and substantially non-elastomeric material, but may alternatively be composed of an elastomeric material which is operably assembled or otherwise incorporated into the fastening tab structure.

In the various embodiments of the invention, fastening tab 44 can be configured to provide an adhesive fastening mechanism. More particularly, the user bond section 52 of fastening tab 44 can include a layer of primary adhesive 54 disposed across an appointed attaching surface 68 of fastening tab substrate 48. The adhesive is configured to provide a desired level of adhesion and securement when applied against the appointed landing zone region of the article. In addition, the adhesive can be configured to be capable of being removed and refastened one or more times onto the appointed landing zone region. An example of a suitable refastenable taping system is described in U.S. Pat. No. 5,147,347 issued Sep. 15, 1992 to Y. Huang et al., the disclosure of which is hereby incorporated by reference to the extent that it is consistent herewith.

In various alternative configurations of the invention, the fastening means may be provided by interlocking, mechanical-type fasteners such as hooks, buckles, snaps, buttons and the like. In particular aspects of the invention the fastening means can be provided by a hook-and-loop fastener system, a mushroom-and-loop fastener system or the like (hereinafter hook-and-loop fastener). Such fastening systems generally comprise a "hook" component and a cooperating "loop" component which engages and interlocks with the hook component. Such systems are, for example, available under the VELCRO trademark. Examples of suitable hook-and-loop fastening systems are described in U.S. Pat. No. 5,019,073 issued May 28, 1991 to T. Roessler et al., the disclosure of which is hereby incorporated by reference to the extent that it is consistent herewith. In a typical configuration of a hook-and-loop fastening system, a portion of hook material is operably connected to the attaching surface 68 of fastening tab substrate 48, and the loop material is employed to construct a cooperating landing zone 46. The landing zone patch, for example, can be suitably attached to the appointed landing zone region on the outside surface of backsheet 22. An alternative configuration of a suitable hook-and-loop fastening system may have the loop material secured to the attaching surface 68 of fastening tab substrate 48. Accordingly, a region of hook material would be employed to form landing zone patch 46.

Fastening tab 44 can advantageously have a stiffness value which is different than the stiffness value of stress beam 98. As a result, fastening tab 44 can be selectively configured with a user bond section 52 which is capable of being fastened, removed and refastened without excessively distorting or tearing the appointed landing zone region of the article. The selective tailoring of the characteristics of fastening tab 44 can be accomplished while retaining the desired stress beam characteristics of stress beam section 98. The stress beam section retains its ability to spread forces across the free end length 94 of side panel 90 without adversely affecting the fastening and refastening capability of fastening tab 44.

In particular aspects of the invention, the user bond end section 60 of fastening tab 44 can have an end length 62 which is greater than the length 66 of the intermediate section 64 of the fastening tab, as representatively shown in FIG. 2. In the illustrated embodiment, for example, the end length can correspond to the widest length dimension of the user bond section 52 of the fastening tab. In other aspects of the invention, the length 62 of end section 60 can also be greater than the length 58 of base section 56 of the fastening tab.

More particularly, end length 62 can be at least about 10 percent greater than intermediate length 66. Alternatively, the end length can be at least about 20 percent greater than the intermediate length, and optionally can be at least about 40 percent greater than the intermediate length. In other aspects of the invention, end length 62 can be not more than about 500 percent greater than intermediate length 66. Alternatively, the end length 62 is not more than about 100 percent greater than intermediate length 66, and optionally is not more than about 60 percent greater than the intermediate length.

End length 62 can be at least about 2 percent greater than base length 58. Alternatively, end length 62 can be at least about 20 percent greater than base length 58, and optionally can be at least about 40 percent greater than the base length. In other aspects, end length 62 can be not more than about 500 percent greater than base length 58. Alternatively, end length 62 can be not more than about 100 percent greater than base length 58, and optionally is not more than about 60 percent greater than the base length of the fastening tab to provide desired performance.

In the illustrated embodiment, for example, intermediate section 64 of fastener tab 44 can be configured to provide an expanding area of the fastener tab. The expanding area provides a gradual transition between base length 58 and end length 62. To avoid the generation of excessive stress concentrations that might initiate undesired fractures, the transition area is substantially free of sharp notches or abrupt angles.

The relatively smaller base and/or intermediate lengths of tab 44 can advantageously contribute to the improved performance provided by the invention. The relatively larger length at the end portion of the user bond section 52 helps provide for a larger user bonding area which can improve the security of the fastening system. At the same time, the relatively smaller length at the base and/or intermediate portions of tab 44 can provide for a relatively greater ease of bending and/or twisting or other movement, as compared to the user bond portion of the tab. As a result, the fastening securement can be maintained at high levels while allowing substantially continual, dynamic fit adjustments at the points of interconnection between the front and rear waistband sections of the article.

Figure 3:
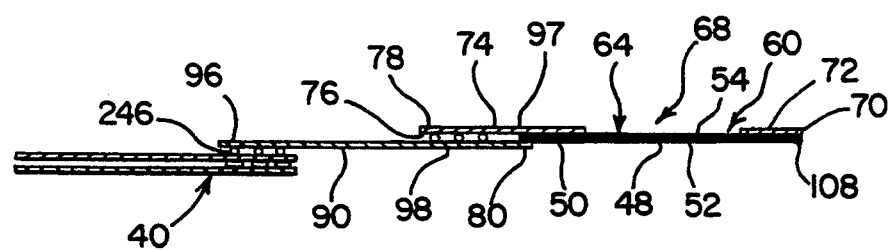
FIG. 3 representatively shows a cross-sectional view of the fastening system illustrated in FIG. 2.

With reference to FIGS. 2 and 3, a tape fastener tab 44 can comprise a tape substrate member 48 having the desired fastening means, such as primary adhesive layer 54, located and disposed on a major facing surface thereof, such as surface 68. The fastener tab provides a factory-bond section 50 for connecting the tape substrate member to a selected portion of diaper 20, and a user-bond section 52 for connecting and securing the waistband sections of the diaper about the body of a wearer. In a particular aspect of the invention, the factory-bond section of fastener tab 44 is attached to the free end region 92 of side panel 90, and is constructed and configured to provide stress beam section 98.

The factory-bond region 50 of tape fastener 44 is appointed for securement onto the desired section of its associated article during the manufacture of the article. The user-bond region 52 of tape fastener 44 is appointed for securing the article on a wearer during use. The representatively shown embodiment of the tape fastener, for example, has primary adhesive layer 54 applied onto a selected surface thereof to provide an adhesive fastening system. In the illustrated embodiment of diaper 20, the factory-bond region 50 of tape fastener 44 is attached to the lateral ends of rear waistband 40, and the user-bond region 52 of the tape fastener is employed to attach the lateral ends of rear waistband 40 to the corresponding lateral ends of front waistband 38 to secure the diaper about the waist of a child. User-bond section 52 connects to a finger tab 70 which includes a substantially non-attaching grasping section 72 thereof. The grasping section can, for example, comprise a layer of exposed absorbent material, and at least a portion of the exposed absorbent material can be operably positioned and arranged to face in the same direction as an appointed inward face of the tape fastener.

With an adhesive fastening tab, a primary adhesive layer 54 can be disposed upon an appointed inwardly facing surface of substrate member 48. The portion of adhesive positioned on factory-bond 50 can be employed to assemble tape fastener 44 onto diaper 20 during the manufacture of the diaper. The portion of adhesive layer 54 located on user-bond region 52 can be employed to secure the diaper onto an infant. The particular adhesive parameters of adhesive layer 54 can be selected and tailored to meet desired adhesive properties, such as adhesive shear strength and adhesive peel strength.

Suitable materials for constructing fasteners 44, such as sheet materials for constructing substrate member 48 and adhesive materials for constructing layer 54, are available from various manufacturers, such as 3M Company, a business having a Disposable Products Division with offices in the 3M Center, St. Paul, Minn.; and Avery International, a business having a Specialty Tape Division with offices in Painesville, Ohio.

The illustrated embodiment of the tape fastening system includes a release tape member 74 for releasably holding user-bond region 52 of the tape fastener in a storage position which protects the user-bond region of primary adhesive layer 54 against contamination or premature adhesion against other portions of diaper 20. In the illustrated embodiment, release tape 74 is positioned in a superposed, adjacent relation with substrate member 48, and is attached to an interior surface of diaper 20. The representatively shown embodiment of release tape 74 includes an anchor surface 76 and an opposite release surface 78. Anchor surface 76 has disposed thereon a suitable anchor adhesive layer, and release surface 78 has disposed thereon a selected layer of an operable release coating, such as a coating composed of cured (cross-linked) poly dimethyl siloxane (PDMS). Suitable release tapes are commercially available from vendors such as 3M Company and Avery International. For example, suitable release tape materials include the FT-4430 material available from Avery International. The release tape material includes a release surface against which the adhesive bearing surface of the fastening tab can be stored and protected from contamination. The fastening adhesive, however, readily separates from the release surface when desired.

In a particular embodiment of the invention, a terminal end portion of release tape 74 may optionally overlap and adhesively bond to an intermediate section of substrate member 48 along a bond region which traverses across the length of the substrate member. The resultant interconnection between substrate member 48 and release tape 74 provides for a Y-bond which can strengthen the assembly and attachment of tape fastener 44 to the section of diaper 20 that is clamped between release tape 74 and factory-bond region 50 of tape substrate member 48. In other aspects of the invention, release tape 74 can be constructed and configured to provide for stress beam section 98.

The user-bond region of tape substrate member 48 has a distal end section 108 which is appointed for grasping by the user to suitably position and adhere the user-bond region of tape fastener 44 to an appointed tape securement zone of the article. In the illustrated embodiment, for example, the user will typically grasp end section 108 to adhere the tape fastener against landing zone patch 46. Distal end section 108 can be constructed to be non-adhering and non-securing so that the end section can be more easily found and lifted by the user.

In a particular aspect of the invention, tape fastener 44 can include a separate finger tab member 70 connected to substrate end section 60 along an attachment region. In an optional configuration of the invention, finger tab 70 may be constructed by providing a particular physical or chemical treatment applied to end section 60 of substrate member 48. In the illustrated embodiment, for example, the finger tab can be a layer of release tape material. In alternative configurations, the treatment can be configured to impart desired absorbency and/or tactile characteristics to the gripping region of the resultant finger tab. In yet other aspects of the invention, finger tab 70 can be composed of a material which is capable of absorbing selected amounts of contaminants, such as powders, liquids, and creams, which may be carried on the fingers of the user. The material of finger tab 70 may substantially end at the longitudinally terminal edge of the tab substrate member. Alternatively, finger tab 70 may extend beyond the terminal edge of the tape substrate member.

The process of the invention provides a distinctive method for forming a plurality of tape fasteners 44 having an improved shape and configuration. An aspect of the process of the invention can also be configured to provide a plurality of fastener tabs 44 connected to a web of side panel material. In particular configurations the side panel material can be elastomeric. The process can be advantageously employed in-line with an operation for manufacturing a selected article, such as a disposable diaper, incontinence garment, feminine care article, gown, garment or the like. The resultant process can be configured to rapidly form a plurality of individual tape fasteners operably connected to side panel members, and then assemble the panel-and-fastener components to the selected article. The process can also be configured to assemble a release tape component to the article, as desired.

In the process aspect of the invention representatively shown in FIGS. 4 and 4A, a method for forming a plurality of fasteners includes the step of providing a substantially continuous web of substrate material along a selected, longitudinal machine-direction 132. The substrate web has a laterally extending cross direction 134 which is substantially perpendicular to the machine direction, and has laterally opposed, longitudinally extending, first and second side edge regions 142 and 144 thereof. A selected fastening means, such as a layer of primary adhesive 54, is positioned and applied onto a major facing surface 186 of the substrate web 140. A first longitudinally extending web of stiffening material 154 is attached to the major surface of substrate web 140 at a location which is proximate a first side edge region 142 of the substrate web. A second longitudinally extending web of stiffening material 156 is attached to the major surface of substrate 140 at a location which is proximate the second side edge region 144 of substrate web 140. The web of substrate material and the webs of stiffening material thereby form a substrate composite 192. The substrate web is separated along a longitudinally extending medial region thereof, with a substantially regularly undulating serpentine separation line 158 to provide an opposed pair of fastener tab subassemblies 194 and 196. At least one fastener tab subassembly, and preferably both fastener tab subassemblies 194 and 196 can be divided along a plurality of division lines 208 which extend substantially laterally across the at least one assembly to provide a plurality of fastener tab components 166. Each of the fastener tab components has an appointed factory bond region 50 thereof.

In the various aspects and configurations of the invention described herein, the webs of stiffening material can be provided by a first web of release material 182 and a second web of release material 184. Accordingly, with reference to FIGS. 5 and 5A, the web of substrate material 140 has a major facing surface 186 thereof, and has first and second side edge regions 142 and 144, respectively. A component of a primary fastening means, such as a layer of primary adhesive 54, is provided across the major surface of substrate web 140. A first securement surface 188 of a side edge portion of the first web of release material 182 is attached to the first side edge region 142 of the substrate web 140. The first release web 182 has a release surface 232 thereof, which is positioned opposite the securement surface of the release web. The release surface is constructed to releasably connect to the selected component of the primary fastening means. A second securement surface 190 at a side edge region of the second web of release material 184 is attached to the second side edge region 144 of substrate web 140. The second release web 184 has a release surface 234 thereof which is positioned opposite the second securement surface 190. The release surface is constructed to releasably connect to the selected component of the primary fastening means. The substrate web and the first and second release webs thereby form a substrate composite 192. A medial region of the substrate web 140 is separated along a generally longitudinally extending serpentine line 158 to provide at least first and second fastener tab subassemblies 194 and 196.

In the various configurations of the invention, at least one fastener tab subassembly, and preferably both fastener tab subassemblies 194 and 196 can be divided along a plurality of division lines 208 which extend substantially laterally across the at least one assembly to provide a plurality of fastener tab components 166. As representatively shown in FIG. 4C, each of the fastener tab components has an appointed factory bond region 50 thereof which can be employed to operably connect at least one of the fastener tabs to each of a pair of lateral side regions of an appointed waistband portion of an article.

Further aspects of the invention can include the steps of attaching a first longitudinally extending web of side panel material to an outboard side region of the first fastener tab subassembly, and attaching a second longitudinally extending web of side panel material to an outboard side region of the second fastener tab subassembly. In particular configurations, either or both of the side panel webs can be composed of an elastomeric material which is elastically stretchable at least along a cross-direction of the side panel webs. The fastener tab subassemblies can be separated along appropriately selected division lines 164 (FIG. 7) to provide a plurality of panel-and-fastener components which can be operably connected to each of a pair of lateral side regions of an appointed waistband portion of an article. Suitable techniques for such operations are described below.

In the various aspects of the invention described herein, the generally longitudinally extending, substantially regularly undulating, serpentine separation line 158 can optionally and desirably include substantially regularly alternating, longitudinally retroceding portions 168 and 170 thereof. The retroceding portions of the separation line can be configured to provide for a fastening tab having a seam section 69 which is relatively narrower than the major portion of the user bond section 52 of the fastening tab 44. More particularly, the retroceding portions of the separation line can be arranged to provide the relatively narrower base sections 56 and intermediate sections 64 of the subsequently produced fastening tabs 44. In the shown configurations, serpentine line 158 also includes traversing sections 242 which generally extend laterally along the cross-direction 134 of the process. Serpentine line 158 can be produced by various conventional techniques, such as die-cutting, water-cutting, thermal-cutting and the like.

In one aspect of the invention, the traversing sections 242 of the serpentine line can be configured to extend along a distance which extends to intrude into at least a portion of each release tape web 182 and 184, as representatively shown in FIG. 5. As a result, with respect to an individual fastening tab 44, the material from one release tape web helps to provide for the stress beam section 98 associated with the particular fastening tab 44, and the material from the second, oppositely located release tape web provides the material for forming an appropriate finger tab 70 associated with the particular fastening tab 44.

The process of the invention can further be configured to form a plurality of stretch panel fasteners. For example, in an aspect of the invention representatively shown in FIG. 6, a first web of side panel material, such as first a stretchable web 130, can be connected to a laterally outboard side edge region 198 of the tape substrate composite 192 to form a first, panel-and-fastener composite subassembly, such as first subassembly 160. More particularly, the stretchable web can be attached to the substrate web at a location which corresponds with the appointed factory bond regions of the individual fasteners formed from the first composite, fastener tab section 194. A second web of side panel material, such as second stretchable web 136, can be connected to a laterally outboard side edge region 200 of the second substrate composite section 196 to form at least a second, panel-and-fastener composite subassembly, such as subassembly 162. Stretchable web 136 can be attached to the substrate web at a location which corresponds with the appointed factory bond regions of the individual fasteners formed from the second composite, fastener tab section 196. In particular configurations, either or both webs of side panel material can be constructed of an elastomeric material which is elastically stretchable at least along the cross-deckle direction 134 of the method. The panel-and-fastener subassemblies are separated along appropriately selected, cross-directional dividing lines 164 to produce a plurality of individual panel-and-fastener components 166.

Figure 7:
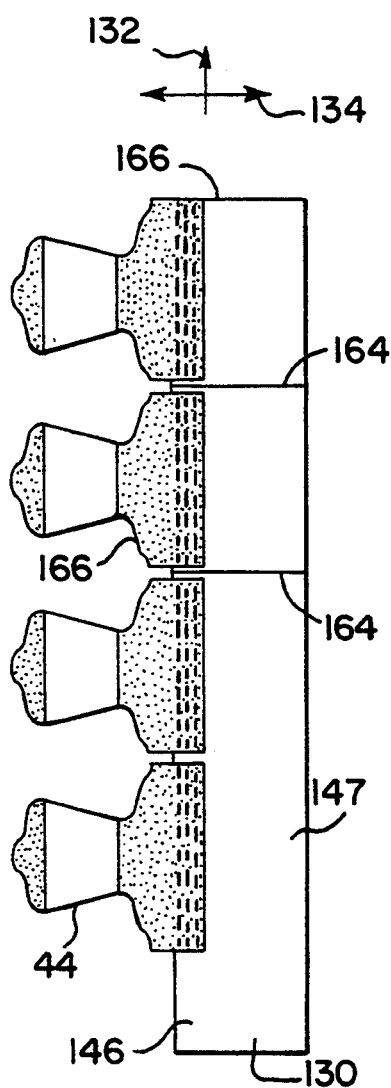
FIG. 7 representatively shows an alternative method for producing a composite web which can be divided into individual panel-and-fastener components.

An alternative aspect of the process of forming a plurality of stretch panel fasteners can be arranged to connect the factory bond regions 50 of a plurality of the fastener tab components 44 to at least one longitudinally extending side edge region 146 of a substantially continuous web of elastomerically stretchable material 130, as representatively shown in FIG. 7. Web 130 is elastomerically stretchable at least along cross direction 134. The elastomerically stretchable web 130 can be severed along a plurality of division lines 164 to provide a plurality of composite panel-and-fastener components 166.

In other aspects of the invention, the factory bond regions 50 of a plurality of fastener tab components 44 can optionally be connected to first and second laterally opposed, longitudinally extending side edge regions 146 and 147 of the elastomerically stretchable web 130. The fastener tab components connected to the first side edge region 146 are offset along machine direction 132 relative to the fastener tab components connected to the second side edge region 147 of web 130. The amount of offset spacing between consecutive, laterally extending centerlines of successive fastener tabs 44 can, for example, generally correspond to the desired extent of an appointed side panel member 90 along the longitudinal direction of the intended article of manufacture.

Figure 8:
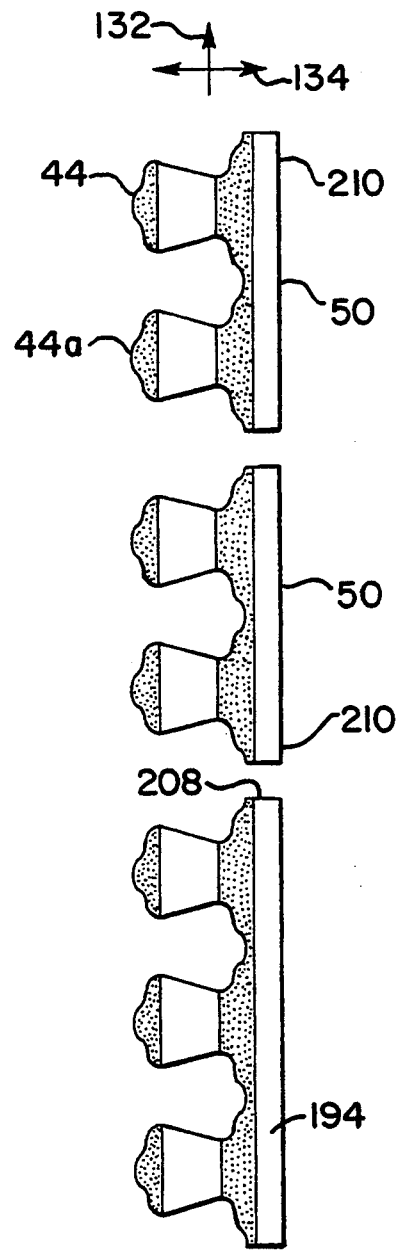
FIG. 8 representatively shows a top plan view of an aspect of the invention which includes the step of forming longitudinally-paired fastener tab sets.

A further aspect of the method of the invention, representatively shown in FIG. 8, includes the step of dividing at least one of the fastener tab subassemblies 194, and preferably both fastener tab subassemblies 194 and 196, along a plurality of division lines 208 which extend substantially laterally across the at least one fastener tab subassembly to provide a plurality of adjacently connected, longitudinally-paired fastener tab component sets 210 having an appointed factory bond regions 50 thereof. The factory bond regions of a plurality of the longitudinally-paired fastener tab sets 210 can be connected to at least one longitudinally extending side edge region 146 of a substantially continuous web of elastomerically stretchable material 130. Elastomeric web 130 can be severed along a plurality of severance lines 164 which extend substantially laterally across the stretchable web and substantially between the adjacently located fastener tabs 44 and 44a forming a fastener tab set 210. The severance lines may optionally have a selected contour, as needed to provide a plurality of composite panel and fastener components 166 having a desired size and shape.

For example, in a particular configuration of the invention representatively shown in FIG. 9, a first plurality of the longitudinally-paired fastener tab component sets 210 can be connected to a first longitudinally extending side edge region 146 of elastomeric web 130 and a second plurality of the longitudinally-paired fastener tab sets 210 can be connected to a second laterally opposed longitudinally extending side edge region 147 of the elastomeric web 130. The fastener tab component sets connected to the first side edge region 147 are offset along machine direction 132 relative to the fastener tab component sets connected to the second side edge region 146. The amount of offset spacing between consecutive, laterally extending centerlines of successive, longitudinally-paired fastener tab sets 210 can, for example, generally correspond to twice the desired extent of an appointed side panel member 90 along the longitudinal direction of the intended final article of manufacture. Alternative configurations of the process can have each of the longitudinally paired fastener tab component sets 210 connected along a single side edge of the elastomeric web 130. The resultant composite assembly can be separated along selected contoured division lines 164 to provide longitudinally-paired, panel-and-fastener components 178.

It should be appreciated that the various steps in the method of the invention can be conducted in various other sequences to arrive at substantially the same result. For example, with reference to FIG. 10, the method for forming a plurality of stretch panel fasteners can include the step of providing a first, substantially continuous web of elastomerically stretchable material 130 extending along a selected, longitudinal machine-direction 132. The first stretchable web 130 is elastomerically stretchable at least along a laterally extending cross direction 134 which is substantially perpendicular to machine direction 132. At least a second, substantially continuous web of elastomerically stretchable material 136 is delivered along machine direction 132. The second web of stretchable material 136 is elastomerically stretchable at least along cross-direction 134, and is laterally spaced from the first web of stretchable material 130 by a selected distance 138 along the cross direction. A substantially continuous web of substrate material 140 is provided along machine direction 132 at a location which is between the first and second webs 130 and 136, respectively, of stretchable material. Substrate web 140 has laterally opposed longitudinally extending side edge regions 142 and 144 thereof. A longitudinally extending lateral side edge region 146 of the first web 130 of stretchable material is attached to the first side edge region 142 of substrate web 140 to provide a first bonded region 148. A longitudinally extending lateral side edge region 150 of the second web 136 of stretchable material is attached to the second side edge region 144 of substrate web 140 to provide a second bonded region 152. A first longitudinally extending web of stiffening material 154 is laid to overlap first bonded region 148, and is operably connected to the first web of stretchable material 130 and to substrate web 140. In particular, the first web of stiffening material 154 can connect to side edge region 146 of stretchable web 130 and to the first side edge region 142 of substrate web 140. A second longitudinally extending web of stiffening material 156 is laid to overlap second bonded region 152, and is operably connected to the second web of stretchable material 136 and to substrate web 140. In particular, stiffening web 156 can connect to side edge region 150 of the second stretchable web and to second side edge region 144 of substrate web 140. Substrate web 140 is separated along a longitudinally extending medial region thereof with a substantially regularly undulating serpentine separation line 158 to provide an opposed pair of composite subassemblies 160 and 162. At least one subassembly, and preferably both subassemblies, are divided along a plurality of division lines 164 which extend substantially laterally across each subassembly to provide a plurality of combined panel-and-fastener components 166.

The overlapping of stiffening webs 154 and 156 can operate to provide for stress beam sections 98 on the individual fastening tabs 44. The material of stiffening webs 154 and 156 can be any material suitable for imparting the desired stiffness level to the appointed stress beam sections 98 of the individual fastening systems. Particular configurations of the invention employ stiffening webs composed of the material employed to provide release tape sections 74 for the individual fastener tabs 44.

In particular arrangements of the invention, the first stiffening web can have an outboard side region thereof which extends laterally beyond and away from the first side edge region 142 of substrate web 140, and the first web of side panel material can be attached to the outboard side region of the first stiffening web to form the first panel-and-fastener subassembly. Similarly, the second stiffening web can have an outboard lateral side region thereof which extends laterally beyond and away from the second side edge region 144 of the substrate web 140, and the second web of side panel material can be attached to the outboard side region of said second stiffening web to form the second panel-and-fastener subassembly.

In the various aspects of the invention described herein, the process can further include the step of securing at least one of the panel-and-fastener components 166 to each of a selected pair of opposed, laterally spaced end regions 172 of appointed waistband sections 174 of an article web 176, as representatively shown in FIG. 11. The article web may, for example, include the material employed to produce back sheet 22 of diaper 20. The article web may also include the material employed to produce the topsheet 24 or other component of the end product article, and may optionally include individual absorbent bodies 26 assembled therewith. A securement 246 (FIG. 14A) may be provided by a suitable attaching mechanism, such as adhesive bonding, thermal bonding, ultrasonic bonding, clips, staples, sewing or the like.

In particular aspects of the invention, at least one composite subassembly 160, and preferably both subassemblies 160 and 162, can be divided along a selected plurality of division lines 164 which are configured and arranged to extend substantially laterally across each subassembly to provide a plurality of longitudinally paired, combined panel-and-fastener components 178 (FIG. 9). At least one of the longitudinally paired panel-and-fastener components 178 can be secured to each of two opposed, laterally spaced side regions 172 of an appointed waistband section 174 of an article web 176 to provide a composite article web 180 (FIG. 11). The composite article web is severed along a cross-direction 134 thereof at a location 206 which operably divides each of the longitudinally paired panel-and-fastener components 178 into two individual panel-and-fastener components 166.

In optional configurations of the invention, the method can include the step of superposing a web of release tape material 182 onto the medial section of substrate web 140. Release tape web 182 is arranged to place release surface 78 against the primary adhesive layer 54 on substrate web 140. In this configuration of the invention, the forming of serpentine separation line 158 severs both substrate web 140 and release tape web 182 during the course of providing the opposed pair of composite subassemblies 160 and 162, or 194 and 196. The securing surface 188 of the release tape web can be employed to anchor the subsequently formed individual release tape members to suitable portions of the final article, such as an inner bodyside surface of diaper 20.

With reference to FIG. 12, the method for forming a plurality of stretch panel fasteners can include the step of providing a first, substantially continuous web of elastomerically stretchable material 130 extending along a selected, longitudinal machine-direction 132. The first stretchable web 130 is elastomerically stretchable at least along a laterally extending cross direction 134 which is substantially perpendicular to machine direction 132. At least a second, substantially continuous web of elastomerically stretchable material 136 is delivered along machine direction 132. The second web of stretchable material 136 is elastomerically stretchable at least along cross-direction 134, and is laterally spaced from the first web of stretchable material 130 by a selected distance 138 along the cross direction. A substantially continuous web of substrate material 140 is provided along machine direction 132 at a location which is between the first and second webs 130 and 136, respectively, of stretchable material. Substrate web 140 has laterally opposed longitudinally extending side edge regions 142 and 144 thereof. A longitudinally extending lateral side edge region 146 of the first web 130 of stretchable material is attached to the first side edge region 142 of substrate web 140 to provide a first bonded region 148. A longitudinally extending lateral side edge region 150 of the second web 136 of stretchable material is attached to the second side edge region 144 of substrate web 140 to provide a second bonded region 152. A first longitudinally extending web of stiffening material 154, such as a first web of spunbond nonwoven fabric or other suitable material, can optionally be laid to overlap first bonded region 148, and is operably connected to the first web of stretchable material 130 and to substrate web 140. In particular, the first web of stiffening material 154 can connect to side edge region 146 of stretchable web 130 and to the first side edge region 142 of substrate web 140. A second longitudinally extending web of stiffening material 156, such as a second web of spunbond nonwoven fabric or other suitable material, can optionally be laid to overlap second bonded region 152, and is operably connected to the second web of stretchable material 136 and to substrate web 140. In particular, stiffening web 156 can connect to side edge region 150 of the second stretchable web and to second side edge region 144 of substrate web 140. Release tape web 182 is delivered and arranged to place release surface 78 against the primary adhesive layer 54 on substrate web 140. Substrate web 140 is separated along a longitudinally extending medial region thereof with a substantially regularly undulating serpentine separation line 158 to provide an opposed pair of composite subassemblies 160 and 162. The forming of serpentine separation line 158 operably severs both substrate web 140 and release tape web 182 during the course of providing the opposed pair of composite subassemblies 160 and 162. At least one subassembly, and preferably both subassemblies, are divided along a plurality of division lines 164 which extend substantially laterally across each subassembly to provide a plurality of combined panel-and-fastener components 166, as representatively shown in FIGS. 12A and 12B.

The securing surface 188 of the release tape web can be employed to anchor the subsequently formed individual release tape members to suitable portions of the final article, such as a selected, inner bodyside surface of diaper 20. As representatively shown in FIGS. 12C and 12D, for example, the release tape 74 can be anchored to a selected surface region of the individual panel-and-fastener component 166. Alternatively, the release tape 74 can be anchored to a selected area of the bodyside surface of topsheet layer 24.

For example, a further aspect of the invention, representatively shown in FIG. 13, generally corresponds to the configuration of the invention shown in FIG. 12, except that the optional steps of providing stiffening webs 154 and 156 are deleted. FIG. 13A illustrates an alternative configuration of the invention which employs a relatively narrower web of release tape material 182. In the arrangement of FIG. 13A, the release tape web overlies the adhesive layer 54, but does not overlap the elastomeric webs 130 and 136.

At least one subassembly 162, and preferably both subassemblies, are divided along a plurality of division lines 164 which extend substantially laterally across each subassembly to provide a plurality of combined panel-and-fastener components 166, as representatively shown in FIGS. 13B and 13C. Similar to the process illustrated in FIG. 12, the configuration of the invention illustrated in FIG. 13 can be arranged to anchor the release tape 74 can be anchored to a selected surface region of the individual panel-and-fastener component 166, as representatively shown in FIGS. 13D and 13E.

Figure 14:
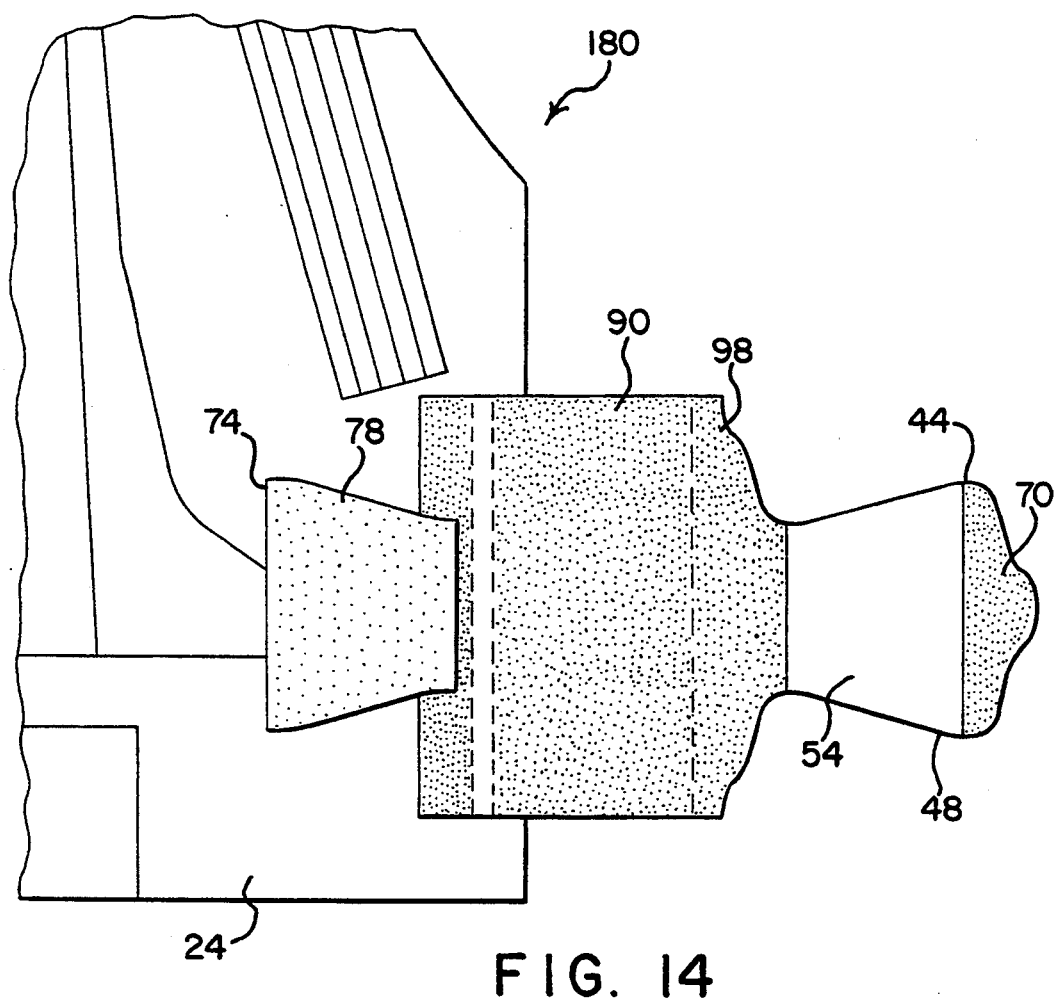
FIG. 14 representatively shows a partial, top plan view of a composite article web wherein a release tape tab is anchored to an inner surface of a topsheet layer of the article web, and wherein the fastener tab has been moved from its storage position on the release tape to a position ready for producing the desired user-bond.
Figure 14A:
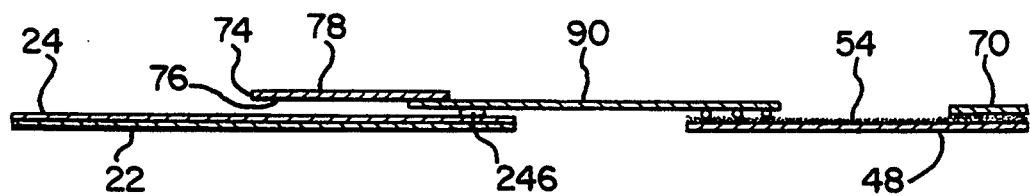
FIG. 14A representatively shows a schematic side elevational view of the composite article web illustrated in FIG. 14.

Alternatively, the release tape 74 can be anchored to a selected area of the bodyside surface of topsheet layer 24 of the composite web 180, as representatively shown in FIG. 14. The Figure illustrates the configuration of fastening tab 44 after the tab has been peeled from the release surface of the release tape 74, and the user-bond adhesive on the tab has been exposed for use. In the storage condition that would typically precede the arrangement shown in FIG. 14, the adhesive bearing, user-bond surface of fastening tab 44 is appropriately arranged such that it can be releasably positioned and held against the release surface of release tape 74. As a result, when side panel 90 is in its storage configuration, the side panel is folded over upon itself to allow for more efficient packaging.

Accordingly, a further aspect of the invention can include the steps of securing at least one of said panel-and-fastener components to each of two laterally opposed end regions 172 of the appointed waistband section 174 of the article web 176 to provide the composite article web 180; and inwardly folding the first and second webs of elastomerically stretchable material 130 and 136 to anchor the securing surface of the release tape material onto a selected surface region of the composite article web.

With reference to FIG. 15, another aspect of the invention can include the step of connecting the first longitudinally extending web of stiffening material 154 is attached to a major facing surface of substrate web 140 at a location which is proximate the first side edge region 142 of the substrate web, and is laterally, inwardly spaced from the first side edge region of the substrate web. In addition, the second longitudinally extending web of stiffening material 156 is attached to a major facing surface of substrate web 140 at a location which is proximate the second side edge region 144 of the substrate web 140, and is laterally, inwardly spaced from the second side edge region of the substrate web.

Figure 16:
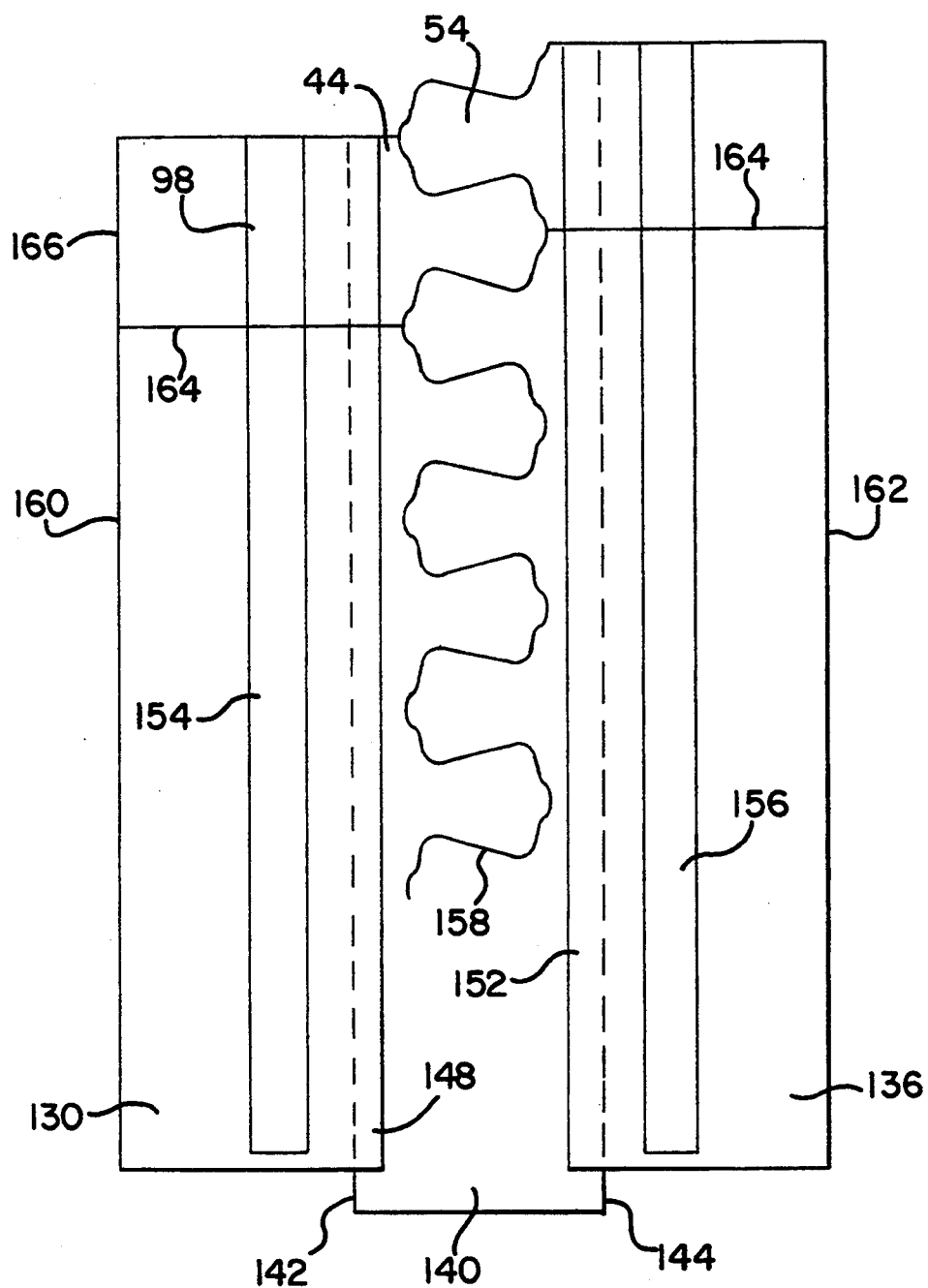
FIG. 16 representatively shows a top plan view of an aspect of the invention which includes the steps of attaching first and second longitudinally extending webs of stiffening material to a major facing surface of first and second elastomeric webs at selected locations which laterally, outwardly spaced from the side edge regions of a medially positioned substrate web.

With reference to FIG. 16, another aspect of the invention can include the step of connecting substrate web 140 between two side panel webs, such as provided by first and second elastomeric webs 130 and 136. The first longitudinally extending web of stiffening material 154 is attached to a major facing surface of elastomeric web 130 at a location which is proximate the first bonded edge region 148 of the elastomeric web 130, and is laterally, outwardly spaced from the first side edge region 142 of the substrate web 140. In addition, the second longitudinally extending web of stiffening material 156 is attached to a major facing surface of elastomeric web 136 at a location which is proximate the second bonded edge region 152 of elastomeric web 136, and is laterally, outwardly spaced from the side edge region 144 of the substrate web 140. Accordingly, the process can be employed to form a fastener system having a stress beam section 98 spaced a selected, discrete distance from the edge of its associated fastener tab 44.

In the various configurations of the invention, the elastomerically stretchable webs 130 and 136 can be composed of any of the materials employed to construct the appointed elastomeric side panels 90. Accordingly, the elastomeric webs can be composed of a stretch-bonded-laminate (SBL) material, a neck-bonded-laminate (NBL) material, an elastomeric film, an elastomeric foam material, or the like. For example, suitable melt-blown elastomeric fibrous webs for forming side panels 90 are described in U.S. Pat. No. 4,663,220 issued May 5, 1987 to T. Wisneski et al., the disclosure of which is hereby incorporated by reference. Examples of composite fabrics comprising at least one layer of nonwoven textile fabric secured to a fibrous elastic layer are described in European Patent Application No. EP 0 110 010 published on Apr. 8, 1987 with the inventors listed as J. Taylor et al., the disclosure of which is hereby incorporated by reference. Examples of NBL materials are described in U.S. Pat. No. 5,226,992 issued Jul. 13, 1993 to Mormon, the disclosure of which is hereby incorporated by reference.

Similarly, substrate web 140 can be composed of any one of the materials suitable for providing fastener tab substrate 48. Accordingly, the substrate web can be composed of a fabric material or a suitable polymer film material, such as polypropylene, polyethylene or other suitable polyolefin. The material comprising substrate web 140 may be opaque, translucent or transparent, as desired, and may include graphics thereon. Optionally, the material may be tinted and/or textured, and may also be selectively embossed. In particular aspects of the invention, substrate web 140 can be constructed of a substantially non-extensible and/or a substantially non-elastomeric material to provide desired benefits.

Release tape webs 182 and 184 can be composed of any of the suitable materials desired for providing release tape 74. Accordingly, the release tape webs can, for example, be composed of a 3M KS-0080 release tape composed of a 3.5 mil thick polypropylene film with a poly dimethylsiloxane release coating and an aliphatic resin. Such release tapes are available from the 3M Company, St. Paul, Minn. It should be readily appreciated that the various webs employed in the method of the invention can be suitably attached to each other employing conventional connecting means. Such connecting means can include, for example, adhesive bonding, thermal bonding, ultrasonic bonding, clips, staples, sewing, or the like, or combinations thereof.

In the various aspects of the invention, the individual fasteners 44 and the individual panel-and-fastener components 166 can be nested within the corresponding fastener tab and composite subassemblies from which the fasteners and panel-and-fastener components are formed. With respect to the individual fastener tabs formed from subassemblies 194 and 196, for example, the fastener tabs formed from subassembly 194 are substantially of equal size and are approximately mirror images of the complementary fasteners formed from subassembly 196. The fasteners tabs produced from nested subassembly 194 are slightly offset from the fasteners produced from nested subassembly 196 by a discrete distance along the length dimension of substrate material 140. More particularly, a nested fastener from subassembly 194 is offset from its opposed counterpart fastener from subassembly 196 by approximately one-half of the desired top-to-bottom span along of an individual tape fastener 44 along the length dimension of the article. In the illustrated embodiment, serpentine separation line 158 stops short of the laterally outboard edges of the finger tab/release tape webs 182 and 184 along cross-direction 134. Optionally, the cross-directional extent of serpentine cut 118 may substantially coincide with the terminal outboard edge boundaries of the finger tab web, or may extend beyond the outboard edge boundaries of the finger tab material.

Having thus described the invention in rather full detail, it will be readily apparent that various changes and modifications can be made without departing from the spirit of the invention. All of such changes and modifications are contemplated as being within the scope of the invention, as defined by the subjoined claims.

We claim:

1. A method for forming a plurality of adhesive fastener assemblies, comprising the steps of:
    (a) providing a web of substrate material along a longitudinal direction, said substrate web having a major facing surface thereof and having first and second side edge regions thereof;
    (b) providing for a component of a primary fastening means disposed across said major surface of said substrate;
    (c) attaching a first web of stiffening material to said substrate web at a location Which is proximate said first side edge region of said substrate web;
    (d) attaching a second web of stiffening material to said substrate web at a location which is proximate said second side edge region of said substrate web; and
    (e) separating a medial region of said substrate web along a generally longitudinally extending serpentine line which extends into said first and second webs of stiffening material to provide at least first and second fastener tab subassemblies.

2. A method as recited in claim 1, further comprising the step of dividing at least one of said first and second fastener tab subassemblies to provide a plurality of fastening tabs.

3. A method as recited in claim 1, further comprising the steps of:
    (f) attaching a first web of side panel material to an outboard side region of said first fastener tab subassembly to form a first composite panel-and-fastener subassembly; and
    (g) attaching a second web of side panel material to an outboard side region of said second fastener tab subassembly to form at least a second composite panel-and-fastener subassembly.

4. A method as recited in claim 3, wherein said attaching step (f) is configured to provide a first web of side panel material composed of an elastomeric material which is stretchable along a cross-direction of said first side panel web; and said attaching step
    (g) is configured to provide a second web of side panel material composed of an elastomeric material which is stretchable along a cross-direction of said second side panel web.

5. A method as recited in claim 4, further comprising the step of dividing at least one of said first and second composite subassemblies to provide a plurality of panel-and-fastener components.

6. A method as recited in claim 5, wherein
said step (c) comprises the step of attaching a first web of stiffening material composed of a first web of release material, said first release web having a first securement surface and having a release surface thereof which is located opposite said securement surface, said release surface constructed to releasably adhere to said component of said primary fastening means; and
said step (d) comprises the step of attaching a second web of stiffening material composed of a second web of release material, said second release web having a second securement surface and having a second release surface thereof which is located opposite said second securement surface, said second release surface constructed to releasably adhere to said component of said primary fastening means.

7. A method as recited in claim 5, further comprising the step of connecting at least one of said panel-and-fastener assemblies to each of a pair of lateral side regions of a waistband portion of an article.

8. A method as recited in claim 7, wherein said separating step (e) is configured to separate said composite along a serpentine line having traversing sections which extend into a portion of each of said release webs.

9. A method as recited in claim 8, wherein said traversing sections of said serpentine line include retroceding portions thereof.

10. A method as recited in claim 1, wherein said providing step (b) includes the step of providing a fastening means which includes a layer of adhesive disposed on said major surface of said web of substrate material.

11. A method as recited in claim 1, wherein said providing step (b) includes the step of having disposed a fastening means comprising a cooperative component of an interlocking mechanical fastener on said major surface of said web of substrate material.

12. A method as recited in claim 11, wherein said disposing step (b) includes the step of having disposed a cooperative hook component of a hook-and-loop type mechanical fastener system on said major surface of said web of substrate material.

13. A method for forming a plurality of stretch panel fasteners, comprising the steps of:
(a) providing a first, substantially continuous web of elastomerically stretchable material extending along a selected, longitudinal machine-direction, said material being elastomerically stretchable at least along a laterally extending cross-direction which is substantially perpendicular to said machine-direction;
(b) providing at least a second, substantially continuous web of elastomerically stretchable material extending along said machine-direction, said material being elastomerically stretchable at least along said cross-direction;
(c) spacing said second web of stretchable material from said first web of stretchable material by a selected distance along said cross-direction;
(d) providing a substantially continuous web of substrate material along said machine-direction at a location which is between said first and second webs of stretchable material, said substrate web having laterally opposed, longitudinally extending side edge regions thereof;
(e) attaching a longitudinally extending lateral side edge region of said first web of stretchable material to said first, side edge region of said substrate web to provide a first bonded region;
(f) attaching a longitudinally extending lateral side edge region of said second web of stretchable material to said second, side edge region of said substrate web to provide a second bonded region;
(g) laying a first longitudinally extending web of stiffening material at a position proximate said first bonded region, and connecting said first stiffening web to at least said first web of stretchable material;
(h) laying a second longitudinally extending web of stiffening material at a position proximate said second bonded region, and connecting said second stiffening web to at least said second web of stretchable material;
(i) separating said substrate web along a longitudinally extending medial region thereof with a substantially regularly undulating serpentine separation line to provide an opposed pair of composite subassemblies;
(j) dividing at least one subassembly along a plurality of division lines which extend substantially laterally across said subassembly to provide a plurality of combined panel-and-fastener components.

14. A method as recited in claim 13, wherein said separating step (e) includes the step of separating said substrate web along said longitudinally extending medial region with a substantially regularly undulating serpentine line having alternating, longitudinally retroceding portions thereof.

15. A method as recited in claim 14, wherein said dividing step (j) includes the step of dividing at least one subassembly along a plurality of division lines which extend substantially laterally across said subassembly to provide a plurality of longitudinally paired, combined panel-and-fastener components.

16. A method as recited in claim 15, further comprising the steps of:
(k) of securing at least one of said longitudinally paired panel-and-fastener components to each of two laterally opposed end regions of an appointed waistband section of an article web to provide a composite article web; and
(l) severing said composite article web along a cross-direction thereof at a location which divides each of said longitudinally paired panel-and-fastener components into two individual panel-and-fastener components.

17. A method as recited in claim 13, wherein
said laying step (g) includes the step of overlapping said first longitudinally extending web of stiffening material over said first bonded region, and connecting said first stiffening web to said first web of stretchable material and to said substrate web; and
said laying step (h) includes the step of overlapping said second longitudinally extending web of stiffening material over said second bonded region, and connecting said second stiffening web to said second web of stretchable material and to said substrate web.

18. A method as recited in claim 17, wherein said dividing step (j) includes the step of dividing at least one subassembly along a plurality of division lines which extend substantially laterally across said subassembly to provide a plurality of longitudinally paired, combined panel-and-fastener components.

19. A method as recited in claim 18, further comprising the steps of:
- (k) of securing at least one of said longitudinally paired panel-and-fastener components to each of two opposed end regions of an appointed waistband section of an article web to provide a composite article web; and
- (l) severing said composite article web along a cross-direction thereof at a location which divides each of said longitudinally paired panel-and-fastener components into two individual panel-and-fastener components.

20. A method for forming a plurality of stretch panel fasteners, comprising the steps of:
- (a) providing a first, substantially continuous web of elastomerically stretchable material extending along a selected, longitudinal machine-direction, said material being elastomerically stretchable at least along a laterally extending cross-direction which is substantially perpendicular to said machine-direction;
- (b) providing at least a second, substantially continuous web of elastomerically stretchable material extending along said machine-direction, said material being elastomerically stretchable at least along said cross-direction;
- (c) spacing said second web of stretchable material from said first web of stretchable material by a selected distance along said cross-direction;
- (d) providing a substantially continuous web of substrate material along said machine-direction at a location which is between said first and second webs of stretchable material, said substrate web having laterally opposed, longitudinally extending side edge regions thereof;
- (e) attaching a longitudinally extending lateral side edge region of said first web of stretchable material to said first, side edge region of said substrate web to provide a first bonded region;
- (f) attaching a longitudinally extending lateral side edge region of said second web of stretchable material to said second, side edge region of said substrate web to provide a second bonded region;
- (g) laying a first longitudinally extending web of stiffening material at a position proximate said first bonded region, and connecting said first stiffening web to at least said first web stretchable material;
- (h) laying a second longitudinally extending web of stiffening material at a position proximate said second bonded region, and connecting said second stiffening web to at least said second web of stretchable material;
- (i) placing a web of release tape material onto said substrate web;
- (j) separating said substrate web and said release tape web along a longitudinally extending medial region thereof with a substantially regularly undulating serpentine separation line to provide an opposed pair of composite subassemblies;
- (k) dividing at least one subassembly along a plurality of division lines which extend substantially laterally across said subassembly to provide a plurality of combined panel-and-fastener components;
- (l) securing at least one of said panel-and-fastener components to each of two laterally opposed end regions of an appointed waistband section of an article web to provide composite article web;
- (m) inwardly folding said first and second webs of elastomerically stretchable material to anchor said release tape material onto a selected surface of said article web.

21. A method as recited in claim 20, wherein said separating step (j) includes the step of separating said substrate web along said longitudinally extending medial region with a substantially regularly undulating serpentine line having alternating, longitudinally retroceding portions thereof.

22. A method as recited in claim 21, wherein
said dividing step (k) includes the step of dividing at least one subassembly along a plurality of division lines which extend substantially laterally across said subassembly to provide a plurality of longitudinally paired, combined panel-and-fastener components,
said securing step (l) includes the step of securing at least one of said longitudinally paired panel-and-fastener components to each of two, laterally opposed end regions of said waistband section of said article web to provide said composite article web; and
further comprising the step of severing said composite article web along a cross-direction thereof at a location which divides each of said longitudinally paired panel-and-fastener components into two individual panel-and-fastener components.

* * * * *